(12) United States Patent
Brooks et al.

(10) Patent No.: US 8,101,628 B2
(45) Date of Patent: Jan. 24, 2012

(54) IMIDAZOLIDINONYL AMINOPYRIMIDINE COMPOUNDS FOR THE TREATMENT OF CANCER

(75) Inventors: Harold Burns Brooks, Carmel, IN (US); Joyce Z. Crich, Indianapolis, IN (US); James Robert Henry, Indianapolis, IN (US); Hong-Yu Li, Zionsville, IN (US); Melissa Kate Slater, Carmel, IN (US); Yan Wang, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 318 days.

(21) Appl. No.: 12/516,514

(22) PCT Filed: Dec. 11, 2007

(86) PCT No.: PCT/US2007/087044
§ 371 (c)(1),
(2), (4) Date: May 27, 2009

(87) PCT Pub. No.: WO2008/076704
PCT Pub. Date: Jun. 26, 2008

(65) Prior Publication Data
US 2010/0076001 A1   Mar. 25, 2010

(51) Int. Cl.
*C07D 401/00*   (2006.01)
(52) U.S. Cl. .......................... 514/275; 544/331
(58) Field of Classification Search ............... 514/210.2, 514/275, 233.5; 544/331, 122
See application file for complete search history.

(56) References Cited

FOREIGN PATENT DOCUMENTS

| WO | 89/07599 | 8/1989 |
|---|---|---|
| WO | WO 2004063192 | 7/2004 |
| WO | WO 2004089913 | 10/2004 |
| WO | WO 2006066172 | 6/2006 |
| WO | WO 2006066172 A1 * | 6/2006 |
| WO | WO 2007092095 | 8/2007 |
| WO | WO 2007117465 | 10/2007 |
| WO | WO 2008076705 | 6/2008 |
| WO | WO 2008144222 | 11/2008 |
| WO | WO 2008144223 | 11/2008 |

OTHER PUBLICATIONS

B.C. Bastian, Genetic Progression From Melanocyte to Malignant Melanoma, in From Melanocytes to Melanoma the Progression to Malignancy 197, 201 (V. J. Hearing et al., eds., 2006).*
S. Cannistra et al, Ovarian Cander, Fallopian Tube Carcinoma and Peritoneal Carcinoma in, 1 Cancer Principles & Practice of Oncology 1568 (V.T. Deviata, Jr. et al. eds., 8th ed., 2008).*
K. G. Chen et al., How Melanoma Cells Evade Chemotherapy, in From Melanocytes to Melanoma the Progression to Malignancy 591 (V. J. Hearing et al., eds., 2006).*
I. Collins, Current Signal Transduction Therapy, 1, 13-23, 13 (2006).*
F.F. De Arruda, et al., Int. J. Radiation Oncology Biol. Phys., 64(2), 363-373 (2006).*
B. Hann et al., Current Opinion in Cell Biology, 13, 778-784 (2001).*
A. Kamb, Nature Reviews Drug Discovery 4, 161-165 (2005).*
S.K. Libutti, Colon Cancer in, Cancer Principles & Practice of Oncology 1232, 1243 (V.T. Deviata, Jr. et al. eds., 8th ed., 2008).*
K. Odunsi et al, Molecular Biology of Gynecological Cancers, in 1 Cancer Principles & Practice of Oncology 1487, 1492 (V.T. Deviata, Jr. et al. eds., 8th ed., 2008).*
K. Odunsi et al, Molecular Biology of Gynecological Cancers, in 1 Cancer Principles & Practice of Oncology 1487, 1492 (V.T. Deviata, Jr. et al. eds., 8th ed., 2008).*
K.P. Olive et al., Clinical Cancer Research 12, 5277-5287 (2006).*
L. Pusztai, Histopathologic and Molecular Markers of Prognosis and Response to Therapy, in Breast Cancer 324, 326-328 (Kelly k. Hunt et al., ed., 2nd ed., 2008).*
A.K. Rustgi, Molecular Biology of the Esophagus and Stomach, in 1 Cancer Principles & Practice of Oncology 989-993, 991 (V.T. DeVita, Jr. et al. eds., 8th ed., 2008).*
N.E. Sharpless et al., Nature Reviews Drug Discovery 5, 741-754, 742 (2006).*
N.F. Smith, Molecular Cancer Therapeutics, 6, 428-440, 428 (2007).*
Y. Song et al., Cancer a Conceptual Framework in, Cancer Principles & Practice of Oncology 1, 5-6 (V.T. Deviata, Jr. et al. eds., 8th ed., 2008).*
A.M. Traynor et al., Drugs of Today, 40(8), 697-710, 698 (2004).*
C. Abad-Zapatero, Drug Discovery Today, 1-8 (2010).*

* cited by examiner

*Primary Examiner* — James O Wilson
*Assistant Examiner* — Alexander R Pagano
(74) *Attorney, Agent, or Firm* — Tina M. Tucker

(57) ABSTRACT

The present invention provides novel imidazolidinonyl aminopyrimidine compounds believed to have clinical use for treatment of cancer through inhibiting Plk1. wherein: $R^1$ hydrogen, hydroxy, halo, methyl, $C_1$-$C_2$ alkoxy, amino, or methylamino; $R^2$ is hydrogen, halo, or cyano; $R^3$ is hydrogen or halo; $R^4$ is hydrogen, halo, or methyl; provided that at least two of $R^1$, $R^2$, $R^3$, and $R^4$ are hydrogen; $R^5$ is hydrogen, halo, or methyl; or a pharmaceutically acceptable salt thereof.

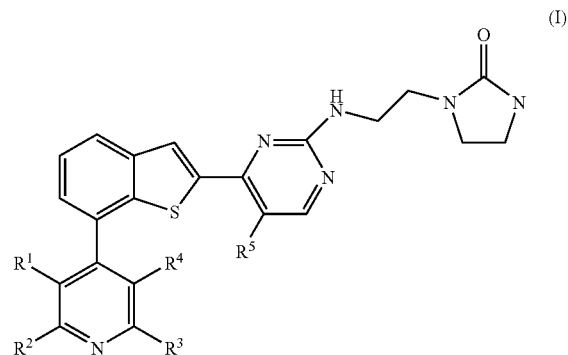

(I)

6 Claims, No Drawings

IMIDAZOLIDINONYL AMINOPYRIMIDINE COMPOUNDS FOR THE TREATMENT OF CANCER

This application claims the benefit under 35 U.S.C. §371 of International Application No. PCT/US2007/087044 filed Dec. 11, 2007 which claims benefit under 35 U.S.C. §119(e) of U.S. Ser. No. 60/871,302 filed Dec. 21, 2006.

BACKGROUND OF THE INVENTION

Plk1 belongs to a small family of protein kinases characterized by a phosphoserine/threonine binding domain known as the polo box domain. Plk1 plays a central role in the regulation of the cell cycle. Among other functions, Plk1 is thought to regulate initiation, progression, and exit from mitosis, the stage when cancer cells divide. Consequently, blocking Plk1 in cancer cells prevents their division or mitosis.

Potent anticancer agents have been identified that interfere with mitosis such as the vinca alkaloids (NAVELBINE®), taxoids (TAXOTERE®) and topoisomerase II inhibitors (ADRIAMYCIN®). VELCADE® is an antineoplastic agent that inhibits the 26S proteosome. However, these drugs cause considerable side effects upon normal, non-dividing cells. Plk inhibitors specifically target dividing cells and may be able to avoid the undesirable toxicities.

Inhibitors of Plk1 are known in the art. See for example, WO 06/066172. Additionally, WO 06/021548 discloses certain dihydropteridinone analogs (e.g., BI-2536) as inhibitors of Plk1. Currently, BI-2536 is in phase II clinical trials but has high clearance (CL >1000 mL/min) and is dose limited by myelosupression in man. There is still a need for further compounds that inhibit Plk1 which possess improved potency or pharmacokinetic properties. It would also be advantageous to have a Plk1 inhibitor that could be dosed orally.

The present invention provides novel imidazolidinonyl aminopyrimidine compounds believed to have clinical use for treatment of cancer through inhibiting Plk1. Certain of these compounds are believed to have improved potency over compounds disclosed in WO 06/066172. Additionally, certain of these compounds are believed to have improved pharmacokinetic properties over BI-2536. Further, due to the oral bioavailability of the compounds of the present invention that were tested, it is believed that certain of these compounds could be dosed orally.

BRIEF SUMMARY OF THE INVENTION

The present invention provides compounds of Formula I:

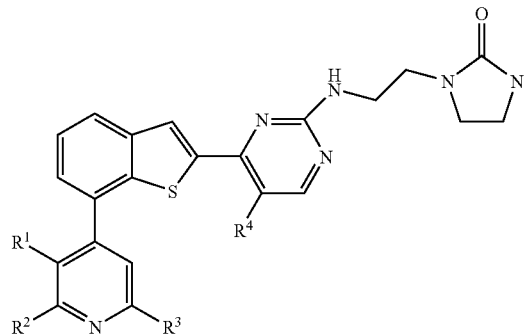

Formula I wherein:

$R^1$ hydrogen, hydroxy, hydroxymethyl, halo, methyl, fluoromethyl, $C_1$-$C_2$ alkoxy, amino, or methylamino;

$R^2$ is hydrogen, halo, or cyano;

$R^3$ is hydrogen or halo;

provided that at least one of $R^1$, $R^2$, and $R^3$ is hydrogen; and $R^4$ is hydrogen, halo, or methyl; or a pharmaceutically acceptable salt thereof.

The present invention provides a method of treating cancer selected from the group consisting of non-small cell lung, oropharyngeal, oesophageal, gastric, melanoma, epidermoid carcinoma of the skin, breast, ovarian, endometrial, colorectal, neuroglioma, glioblastoma, thyroid carcinoma, cervical, pancreatic, prostate, hepatoblastoma and non-Hodgkin lymphoma cancers in a mammal comprising administering to a mammal in need of such treatment an effective amount of a compound of Formula I or a pharmaceutically acceptable salt thereof.

The present invention also provides a pharmaceutical composition comprising a compound of Formula I or a pharmaceutically acceptable salt thereof, in combination with a pharmaceutically acceptable excipient, carrier, or diluent.

This invention also provides a compound of Formula I or a pharmaceutically acceptable salt thereof for use in the preparation of a medicament. Additionally, this invention provides a compound of Formula I or a pharmaceutically acceptable salt thereof for use in the preparation of a medicament for the treatment of cancer in mammals, selected from the group consisting of non-small cell lung, oropharyngeal, oesophageal, gastric, melanoma, epidermoid carcinoma of the skin, breast, ovarian, endometrial, colorectal, neuroglioma, glioblastoma, thyroid carcinoma, cervical, pancreatic, prostate, hepatoblastoma and non-Hodgkin lymphoma cancers. Furthermore, this invention provides a pharmaceutical composition adapted for the treatment of cancer selected from the group consisting of non-small cell lung, oropharyngeal, oesophageal, gastric, melanoma, epidermoid carcinoma of the skin, breast, ovarian, endometrial, colorectal, neuroglioma, glioblastoma, thyroid carcinoma, cervical, pancreatic, prostate, hepatoblastoma and non-Hodgkin lymphoma cancers comprising a compound of Formula I or a pharmaceutically acceptable salt thereof in combination with one or more pharmaceutically acceptable excipients, carriers, or diluents.

The present invention also provides compounds of the Formula:

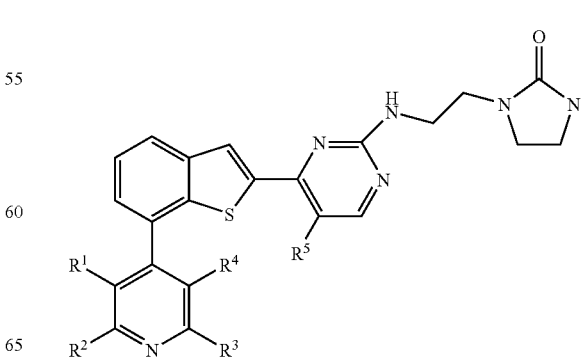

wherein:

R[1] hydrogen, hydroxy, halo, methyl, $C_1$-$C_2$ alkoxy, amino, or methylamino;
R[2] is hydrogen, halo, or cyano;
R[3] is hydrogen or halo;
R[4] is hydrogen, halo, or methyl;
provided that at least two of R[1], R[2], R[3], and R[4] are hydrogen;
R[5] is hydrogen, halo, or methyl; or
a pharmaceutically acceptable salt thereof.

DETAILED DESCRIPTION OF THE INVENTION

The general chemical terms used in the formulae above have their usual meanings. For example, the term "($C_1$-$C_2$) alkoxy" means methoxy and ethoxy. The term "halo" means fluoro, chloro, bromo, and iodo.

It will be understood by the skilled reader that most or all of the compounds of the present invention are capable of forming salts. The compounds of the present invention are amines, and accordingly react with any of a number of inorganic and organic acids to form pharmaceutically acceptable acid addition salts. Such pharmaceutically acceptable acid addition salts and common methodology for preparing them are well known in the art. See, e.g., P. Stahl, et al., HANDBOOK OF PHARMACEUTICAL SALTS: PROPERTIES, SELECTION AND USE, (VCHA/Wiley-VCH, 2002); S. M. Berge, et al., "Pharmaceutical Salts," *Journal of Pharmaceutical Sciences*, Vol 66, No. 1, January 1977.

Preferred are compounds of Formula I wherein:
a) R[1] is hydrogen or methyl;
b) R[2] is hydrogen or halo;
c) R[3] is hydrogen or halo;
d) R[4] is halo;
e) R[4] is methyl;
f) R[4] is hydrogen;
g) R[1] is hydrogen, R[2] is chloro, R[3] is hydrogen, and R[4] is hydrogen;
h) R[1] is methyl, R[2] is hydrogen, R[3] is fluoro, and R[4] is fluoro; and
i) R[1] is methyl, R[2] is hydrogen, R[3] is fluoro, and R[4] is methyl;

Schemes

The skilled artisan will appreciate that not all of the substituents in the compounds of the present invention will tolerate certain reaction conditions employed to synthesize the compounds. These moieties may be introduced at a convenient point in the synthesis, or may be protected and then deprotected as necessary or desired. The skilled artisan will appreciate that the protecting groups may be removed at any convenient point in the synthesis of the compounds of the present invention. Methods for introducing and removing nitrogen and oxygen protecting groups are well known in the art; see, for example, Greene and Wuts, *Protective Groups in Organic Synthesis*, 3rd Ed., John Wiley and Sons, New York, Chapter 7 (1999). Furthermore, the skilled artisan will appreciate that in many circumstances, the order in which moieties are introduced is not critical. The particular order of steps required to produce the compounds of the present invention can be dependent upon the particular compound being synthesized, the starting compound, and the relative lability of the substituted moieties.

Compounds of the present invention can be prepared by carrying out at least two variants discussed below. In the schemes below all substituents, unless otherwise indicated, are as previously defined and suitable reagents are well known and appreciated in the art. In Scheme 2, Y is halo and Z is boronic acid.

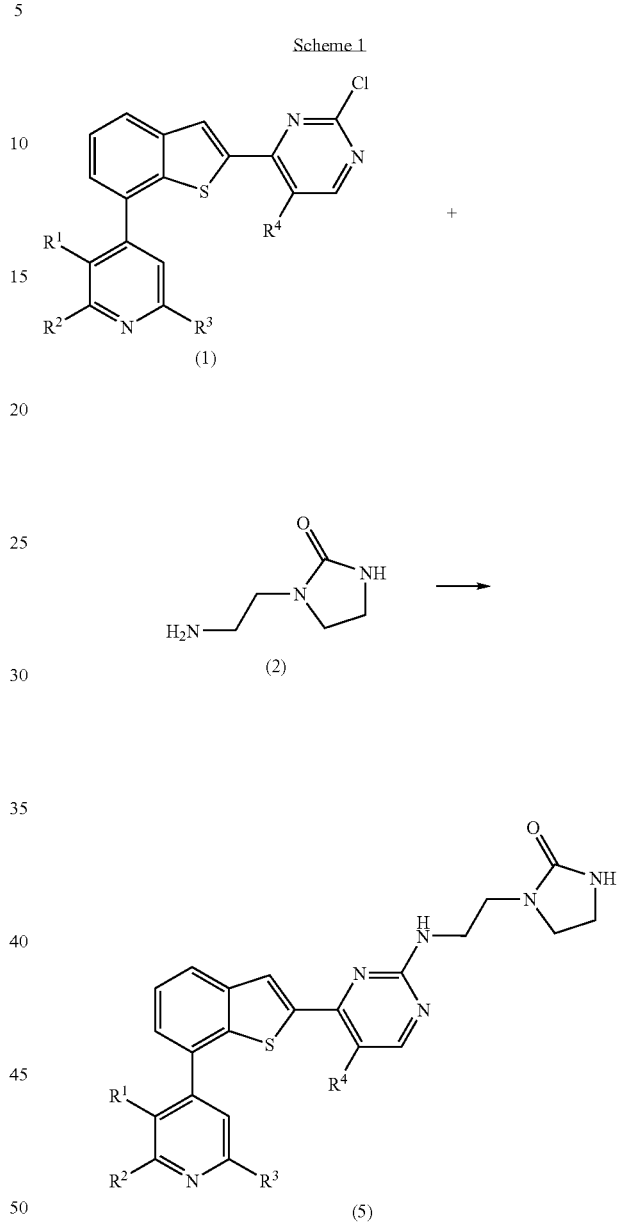

A compound of Formula (1) is reacted with 2-(amino-ethyl)-1,3-dihydro-imidazol-one (2) to give a compound of Formula (5) via a nucleophilic displacement reaction. Such reactions are carried out in a suitable solvent, such as n-butanol, dioxane, N-methylpyrrolidin-2-one (NMP), and the like. Generally, the reactions are carried out at temperatures of from about 120° C. to 150° C. using an oil bath or a microwave reactor. Typical stoichiometry for this reaction is based on the compound of Formula (3) and about 2 equivalents of 2-(amino-ethyl)-1,3-dihydro-imidazol-one are used Amine bases, such as triethyl amine, diisopropylethyl amine, and the like, can be used.

Scheme 2

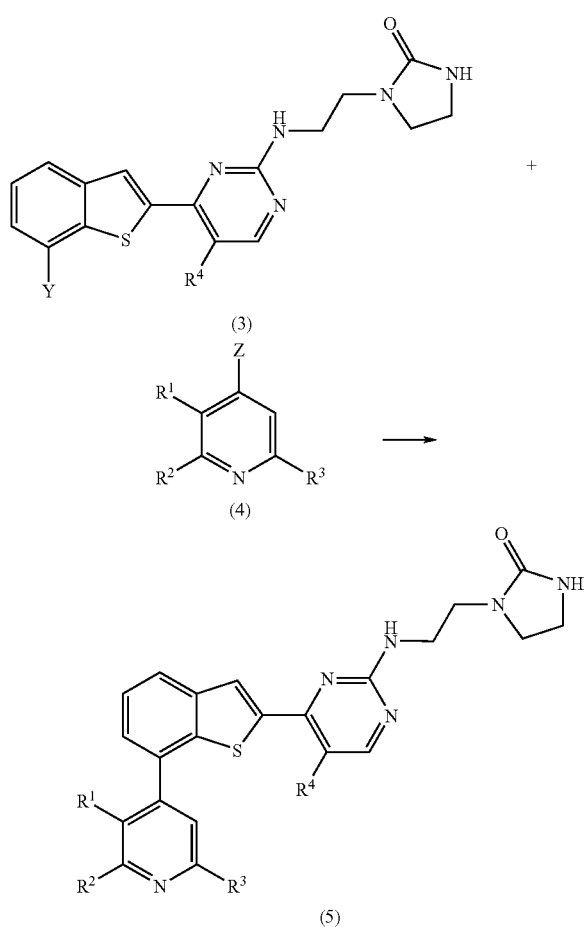

A compound of Formula (3) is reacted with a compound of Formula (4) in a Suzuki reaction using a suitable palladium catalyst, such as tetrakis(triphenylphosphine)palladium(0), [1,1'-bis(diphenylphosphino)ferrocene]dichloropalladium (II), and the like in the presence of a base, such as sodium carbonate, potassium carbonate, and the like. Such reactions are carried out in a suitable solvent, such as THF, dioxane, water, and the like. Generally, the reactions are carried out at temperatures of from about 100° C. to 150° C. using an oil bath or a microwave reactor.

In an optional step, a pharmaceutically acceptable salt of a compound of the present invention is formed. The formation of such salts is well known and appreciated in the art.

As will be readily appreciated compounds of Formulas (1) and (3) can be readily prepared by methods similar to those described herein by procedures that are well-known and established in the art. For example, compounds of Formula (1) are prepared by coupling an optionally substituted pyridinyl compound with an optionally substituted benzothiophenyl compound by Suzuki coupling methods, as described above. The resulting Suzuki adduct is boronylated by methods well known in the art and further coupled to an optionally substituted pyrimidine halide via Suzuki coupling methods, as described above. Compounds of Formula (3) are prepared by boronylation of an optionally substituted benzothiophenyl compound by methods well known in the art followed by addition of 2-(amino-ethyl)-1,3-dihydro-imidazol-one (2) to the resulting boronic acid/ester via nucleophilic aromatic substitution. Also, it is recognized that the steps required to prepare a compound of Formula (1) or (3) can be carried out in any order including reaction of a partial compound of Formula (1) or (3) with a compound of Formula (2) and/or Formula (4), such that the later carried out carbon-carbon bond formation, coupling reaction, etc, provide a compound of the present invention.

The present invention is further illustrated by the following examples and preparations. These examples and preparations are illustrative only and are not intended to limit the invention in any way. The terms used in the examples and preparations have their normal meanings unless otherwise designated. The example compounds below were named using ChemDraw®, Version 10.

Preparation 1

2-Benzo[b]thiophen-7-yl-4,4,5,5-tetramethyl-[1,3,2]dioxaborolane

Combine 7-bromo-benzo[b]thiophene (426 mg, 2 mmol), bis(pinacolato)diboron (756 mg, 3 mmol), [1,1'-bis(diphenylphosphino)ferrocene]dichloropalladium(II), complex with dichloromethane (1:1) (81 mg, 0.1 mmol), potassium acetate (294 mg, 3 mmol) in dimethyl sulfoxide (DMSO) (10 mL) in a flask. Bubble nitrogen through the mixture for 5 min. Seal the flask and heat in an oil bath at 100° C. for 4 hours. Dilute the mixture with chloroform/isopropanol (3/1). Wash the solution with saturated aqueous sodium chloride. Dry the solution over sodium sulfate. Concentrate the solution in vacuo to a dark residue. Purify by column chromatography (hexane to 20% ethyl acetate in hexane) to afford the title compound (342 mg, 66%) as a colorless solid. MS (ES) m/z 261 [M+1]$^+$.

Preparation 2

Benzo[b]thiophene-7-boronic acid

Combine 7-bromobenzo[b]thiophene (300 g, 1.41 mmol) and triisopropylborate (403.6 g, 2.15 mmol) in anhydrous tetrahydrofuran (THF) (4000 mL) in a 12 L Morton flask fitted with a mechanical stirrer and cool under nitrogen in a dry-ice/acetone bath to −70° C. Add n-butyl lithium (1.6 M in hexane, 714 g, 1.68 mmol) dropwise at such a rate as to keep the internal temperature less than −67.5° C. After the addition is complete, allow the reaction mixture to stir at this temperature for 1 hour. Remove the cooling bath and slowly add 4 L of water. Add concentrated HCl (75 mL) until the pH of the solution is about pH=2. Allow the slurry to stir for 1 hour. Add sufficient 5 N aqueous NaOH to adjust the pH of the mixture to about pH=12. Separate the layers and save the aqueous layer. Dilute organic layer with 4 L of methyl-tert-butyl ether and extract with 1 L of 5 N aqueous NaOH. Separate the layers. Combine the aqueous layer with the previous aqueous extract. Wash the aqueous layer with additional methyl-tert-butyl ether (4 L). Separate the layers and transfer the aqueous layers to a 12 L 3-neck round bottom flask fitted with a mechanical stirrer. Cool the solution to +5° C. with an ice-water bath. Add concentrated HCl slowly until the pH of the solution is about pH=2. Stir the mixture for 30 min and filter off the resulting solid. Rinse the solid on the funnel twice with 2 L of water and allow to air-dry for 30 min. Place the solid in a vacuum oven at 50° C. and dry under vacuum overnight. Remove the yellow color by slurrying the dried solid with 2 L of n-heptane for 30 min. Again filter off the solid, air-dry for 30 min, and vacuum dry at 40° C. overnight to afford the title compound (188.8 g, 75%) as a white solid. ¹H NMR (400 MHz, CD₃OD) δ 7.86 (d, J=8 Hz, 1H), 7.49-7.57 (m, 2H), 7.30-7.39 (m, 2H).

Preparation 3

(6-Fluoro-pyridin-3-yl)-carbamic acid tert-butyl ester

Equip a 100 mL 3 neck round bottom flask with: a magnetic stirrer, a thermocouple controlled heating mantle, a condenser, and a nitrogen atmosphere. Charge 5-amino-2-fluoropyridine (5 g, 44.6 mmol), THF (50 mL), 4-dimethylaminopyridine (549 mg, 4.5 mmol, 10 mol %), and di-tert-butyl-dicarbonate (10.7 g, 49 mmol). Heat the mixture to 50° C. for 4 hours. Cool and concentrate in vacuo. Dissolve residue into dichloromethane/water and filter. Transfer filtrate to a separatory funnel and separate the dichloromethane layer. Dry the dichloromethane over sodium sulfate, filter and concentrate in vacuo. Chromatograph on silica eluting with an isocratic mixture of 10% isopropanol/90% dichloromethane to give the title compound (1.64 g, 17%) as a tan, clear oil that solidifies upon vacuum drying. MS (EI) m/z 261 M.

Preparation 4

(2-Fluoro-pyridin-3-yl)-carbamic acid tert-butyl ester

Prepare the title compound essentially according to the preparation of (6-fluoro-pyridin-3-yl)-carbamic acid tert-butyl ester using the appropriate starting material. GCMS (EI) m/z 212 M.

Preparation 5

N-(4-Iodo-pyridin-3-yl)-2,2-dimethyl-propionamide

Equip a 250 mL 3-neck round bottom flask with: a magnetic stirrer, a thermocouple, a dry ice/acetone bath, a nitrogen atmosphere, and an addition funnel. Charge 2,2-dimethyl-N-pyridin-3-yl-propionamide (3.0 g, 16.8 mmol), diethyl ether (67 mL), tetramethylene diamine (4.68 g, 6.08 mL, 40.3 mmol). Cool the reaction to -78° C. Add slowly via glass syringe n-butyllithium (2.5 M solution in hexane, 16.2 mL, 40.3 mmol) over 10 min. Allow the reaction to warm to -13° C. over 2 hours. Cool the reaction to -78° C. Add an iodine solution (8.5 g, 33.6 mmol in 20 mL THF) to the reaction via the addition funnel and mix 2.5 hours at -68° C. Quench the reaction by the addition of saturated aqueous NH₄Cl solution (40 mL). Extract with ethyl acetate (100 mL) and discard the aqueous phase. Wash the organic layer with a saturated aqueous sodium thiosulfate solution (100 mL) and saturated aqueous sodium chloride. Dry the organic phase over sodium sulfate and filter. Concentrate in vacuo to give brown oil. Chromatograph on silica (80 g) eluting with a gradient of 100% dichloromethane to 70% ethyl acetate/30% dichloromethane to afford the title compound (1.19 g, 23%). MS (ES) m/z 305 [M+1]⁺

Prepare the following compounds essentially according to the preparation of N-(4-iodo-pyridin-3-yl)-2,2-dimethyl-propionamide using the appropriate starting material.

| Prep | Compound Name | Physical Data |
|---|---|---|
| 6 | (6-Fluoro-4-iodo-pyridin-3-yl)-carbamic acid tert-butyl ester | MS (ES) m/z 339 [M + 1]⁺ |
| 7 | (2-Fluoro-4-iodo-pyridin-3-yl)-carbamic acid tert-butyl ester | GC-MS (EI) m/z 338 M⁺ |

Preparation 8

3-Methoxymethoxy-pyridine

Dissolve 3-hydroxypyridine (7 g, 74 mmol) in THF (20.6 mL) and dimethylformamide (34.4 mL) and cool to -15° C. Add potassium tert-butoxide (8.3 g, 74 mmol) and stir at -15° C. for 30 min. Treat the mixture with chloromethylmethyl ether (5.81 mL, 77 mmol) dropwise over 40 min. After the addition is complete, stir the mixture at -15° C. for an additional hour. Remove the ice bath and allow the mixture to warm slowly to 15° C. Pour the mixture into saturated aqueous sodium chloride and stir vigorously for 10 min. Extract the resulting solution with three portions of ethyl acetate. Combine the organic extracts and wash with saturated aqueous sodium chloride, dry over sodium sulfate, filter, and concentrate in vacuo. Use the resulting product without further purification. ¹H NMR (400 MHz, CDCl₃) δ 8.42 (d, J=3 Hz, 1H), 8.28 (d, J=5 Hz, 1H), 7.37-7.42 (m, 1H), 7.21-7.27 (m, 1H), 5.20 (s, 2H), 3.49 (s, 3H).

Preparation 9

2-Chloro-5-methoxymethoxy-pyridine

Suspend sodium hydride (3.7 g, 93 mmol) in DMF (50 mL) and add a solution of 2-chloro-5-hydroxypyridine (10 g, 77 mmol) in DMF (20 mL) dropwise over 45 min. Stir the resulting solution at room temperature for 1.5 hours. Add chloromethylmethyl ether (6.6 mL, 86 mmol) dropwise over 45 min. Stir the resulting mixture at room temperature for 12 hours. Dilute the mixture with ethyl acetate, water, and saturated aqueous sodium chloride. Isolate the organic solution and wash with three portions of water, one portion of saturated aqueous sodium chloride, dry over sodium sulfate, filter, and concentrate in vacuo. Purify the crude product by column chromatography on 330 g of silica gel eluting with a gradient from hexane to 30% ethyl acetate in hexane over 20 min and then hold at 30% ethyl acetate in hexane for 30 min to give the title compound (10.8 g, 81%) as a clear oil. MS (ES) m/z 174.0 [M+1]⁺.

Prepare the following intermediate with methods similar to those used for 2-chloro-5-methoxymethoxy-pyridine.

| Prep | Compound Name | NMR |
|---|---|---|
| 10 | 2-Fluoro-5-methoxymethoxy-pyridine | ¹H NMR (400 MHz, CDCl₃) δ 3.48 (s, 3H), 5.15 (s, 2H), 6.85 (dd, J = 3.6 Hz, J = 8.8 Hz, 1H), 7.47 (m, 1H), 7.96 (m, 1H) |

Preparation 11

2-Chloro-4-iodo-5-methoxymethoxy-pyridine

Add tert-buty lithium (1.7 M in pentane, 72 mL, 123 mmol) to a solution of 2-chloro-5-methoxymethoxy-pyridine (10.8 g, 62 mmol) in THF (300 mL) at −70° C. dropwise over 10 min. Stir the resulting solution at −70° C. for 30 min. Add a solution of iodine (23 g, 92 mmol) in THF (150 mL) dropwise over 30 min. Stir the resulting solution at −70° C. for 1 hour. Remove the ice bath and allow the reaction to warm to room temperature. Dilute the mixture with ethyl acetate and water and isolate the phases. Extract the aqueous phase with two portions of ethyl acetate. Combine the organic extracts and wash with two portions of aqueous sodium thiosulfate, one portion of water, one portion of saturated aqueous sodium chloride, dry over sodium sulfate, filter and concentrate in vacuo. Triturate the resulting solid with hexane. Collect the solid by vacuum filtration and wash the solid with hexane. Dry the solid under vacuum to give the title compound (10.8 g, 58%) as a brown solid. $^1$H NMR (400 MHz, DMSO-$d_6$) δ 8.08 (s, 1H), 7.98 (s, 1H), 5.43 (s, 2H), 3.40 (s, 3H).

Prepare the following intermediate using essentially the procedure for 2-chloro-4-iodo-5-methoxymethoxy-pyridine.

| Prep | Compound Name | NMR |
|---|---|---|
| 12 | 2-Fluoro-4-iodo-5-methoxymethoxy-pyridine | $^1$H NMR (400 MHz, CDCl$_3$) δ 3.53 (s, 3H), 5.23 (s, 2H), 7.39 (d, J = 4.0 Hz, 1H), 7.96 (d, J = 1.6 Hz, 1H) |

Preparation 13

6-Chloro-4-iodo-pyridin-3-ol

Treat a solution of 2-chloro-4-iodo-5-methoxymethoxy-pyridine (8.1 g, 27 mmol) in THF (40 mL) with 3 N HCl (61 mL). Heat the resulting mixture to 60° C. for 3 hours. Cool the mixture to room temperature and adjust the pH to 7 by the slow addition of saturated aqueous sodium bicarbonate solution. Extract the mixture with three portions of ethyl acetate. Combine the organic extracts and dry over sodium sulfate, filter, and concentrate in vacuo to give the title compound (6.8 g, 98%) as a brown solid used without further purification. $^1$H NMR (400 MHz, DMSO-$d_6$) δ 11.04 (s, 1H), 7.81-7.87 (m, 2H).

Prepare the following intermediate using essentially the procedure for 6-chloro-4-iodo-pyridin-3-ol.

| Prep | Compound Name | MS (ES) [M + 1]$^+$ |
|---|---|---|
| 14 | 6-Fluoro-4-iodo-pyridin-3-ol | 240 |

Preparation 15

2-Chloro-5-ethoxy-4-iodo-pyridine

Treat a solution of 6-chloro-4-iodo-pyridin-3-ol (4.9 g, 19 mmol) and potassium carbonate (8.0 g, 58 mmol) in dimethylformamide (50 mL) with ethyl iodide (4.7 mL, 58 mmol). Heat at 60° C. for 3 hours. Cool the mixture to room temperature and filter.

Dilute the mixture with ethyl acetate and wash with a 10% aqueous citric acid solution. Combine the aqueous solutions and extract with two additional portions of ethyl acetate. Combine the organic extracts and wash with three portions of water, one portion of saturated aqueous sodium chloride, dry over sodium sulfate, filter, and concentrate in vacuo to give the title compound (5.1 g, 93%) as a brown solid used without further purification. $^1$H NMR (400 MHz, DMSO-$d_6$) δ 8.00 (s, 1H), 7.93 (s, 1H), 4.18 (q, J=7 Hz, 2H), 1.35 (t, J=7 Hz, 3H).

Preparation 16

4-Benzo[b]thiophen-7-yl-2-chloro-pyridine

In a flask, combine 7-bromo-benzo[b]thiophene (1.7 g, 12 mmol), 2-chloro-4-(4,4,5,5-tetramethyl-[1,3,2]dioxaborolan-2-yl)-pyridine (1.6 g, 7 mmol), [1,1'-bis(diphenylphosphino)ferrocene]dichloropalladium(II), complex with dichloromethane (1:1) (285 mg, 0.3 mmol), 2-(di-tert-butylphosphino)biphenyl (63 mg, 0.2 mmol), sodium carbonate (2 M, 8 mL, 16 mmol) and THF (20 mL). Heat the mixture at 100° C. for 3 hours. Dilute the mixture with chloroform/isopropanol (3/1). Wash the solution with saturated aqueous sodium chloride. Dry over sodium sulfate. Concentrate the solution in vacuo to a dark residue. Purify by column chromatography (dichloromethane to 20% THF in dichloromethane) to afford the title compound (1.14 g, 66%) as a yellow solid. MS (ES) m/z 246 [M+1]$^+$.

Prepare the following compounds by methods similar to those used for 4-benzo[b]thiophen-7-yl-2-chloro-pyridine using DMSO.

| Prep | Compound Name | MS (ES) [M + 1]$^+$ | Comments |
|---|---|---|---|
| 17 | 4-Benzo[b]thiophen-7-yl-pyridine | 212 | Heat at 100° C. catalyst Pd(PPh$_3$)$_4$ |

Preparation 18

4-Benzo[b]thiophen-7-yl-2-fluoro-5-methyl-pyridine

In a flask, combine 2-fluoro-4-iodo-5-methyl-pyridine (355 mg, 1.5 mmol), 2-benzo[b]thiophen-7-yl-4,4,5,5-tetramethyl-[1,3,2]dioxaborolane (282 mg, 1.8 mmol), [1,1'-bis(diphenylphosphino)ferrocene]dichloropalladium(II), complex with dichloromethane (1:1) (61 mg, 0.07 mmol), 2-(di-tert-butylphosphino)biphenyl (13 mg, 0.04 mmol), sodium carbonate (2 M, 1.5 mL, 3 mmol) and THF (10 mL). Heat the mixture at 100° C. for 3 hours in an oil bath. Dilute the mixture with chloroform/isopropanol (3/1). Wash the solution with saturated aqueous sodium chloride. Dry over sodium sulfate. Concentrate in vacuo to a dark residue. Purify by column chromatography (20% ethyl acetate in hexane) to afford the title compound (300 mg, 82%) as yellow oil. MS (ES) m/z 244 [M+1]$^+$.

Prepare the following intermediates essentially according to the preparation of 4-benzo[b]thiophen-7-yl-2-fluoro-5-methyl-pyridine using the appropriate starting material.

| Prep | Compound Name | Physical Data MS (ES) m/z [M + 1]+ | Comments |
|---|---|---|---|
| 19 | (4-Benzo[b]thiophen-7-yl-6-fluoro-pyridin-3-yl)-carbamic acid tert-butyl ester | 345 | N₂ atmosphere |
| 20 | 4-Benzo[b]thiophen-7-yl-2-fluoro-pyridin-3-ylamine | 345 | N₂ atmosphere |
| 21 | 4-Benzo[b]thiophen-7-yl-2-chloro-5-ethoxy-pyridine | 290 | N₂ atmosphere |
| 22 | (4-Benzo[b]thiophen-7-yl-6-fluoro-pyridin-3-yl)-carbamic acid tert-butyl ester | 345 | Deoxygenated (N₂) |
| 23 | (4-Benzo[b]thiophen-7-yl-pyridin-3-yl)-methyl-carbamic acid tert-butyl ester | 325 | Deoxygenated (N₂) |

Preparation 24

4-Benzo[b]thiophen-7-yl-3-methoxymethoxy-pyridine

Solution A: Treat a solution of 3-methoxymethoxy-pyridine (2.5 g, 18 mmol) in diethyl ether (90 mL) at −70° C. with tert-butyl lithium (1.7 M in pentane, 10 mL, 18 mmol) dropwise over 10 min. Stir the mixture at −70° C. for 40 min and add a solution of triisopropyl borate (5 mL, 22 mmol) in THF (10 mL) dropwise over 5 min. Stir the mixture at −70° C. for one hour and then remove the ice bath and allow the mixture to slowly warm to room temperature.

Solution B: Treat a solution of 7-bromo-benzo[b]thiophene (3.8 g, 18 mmol), 2-(di-tert-butylphosphino)biphenyl (268 mg, 0.90 mmol), [1,1'-bis(diphenylphosphino)ferrocene]dichloropalladium(II), complex with dichloromethane (1:1) (732 mg, 0.90 mmol) in 1,4-dioxane (30 mL) with 2 M aqueous sodium carbonate (72 mL, 36 mmol). Once solution A reaches room temperature, heat the solution to 80° C.

Treat solution B with solution A dropwise over 10 min. Heat the combined solution to 85° C. for 5 hours. Cool the mixture to room temperature and dilute with ethyl acetate and water. Wash the organic phase with water and saturated aqueous sodium chloride, dry over sodium sulfate, filter, and concentrate in vacuo. Purify the crude product by column chromatography on 120 g silica gel eluting with a gradient of dichloromethane to ethyl acetate to give the title compound (3.8 g) containing some starting 3-methoxymethoxy-pyridine. Use product without further purification. ¹H NMR (400 MHz, CDCl₃) δ 8.68 (s, 1H), 8.42 (d, J=4 Hz, 1H), 7.88 (d, J=8 Hz, 1H), 7.33-7.50 (m, 5H), 5.12 (s, 2H), 3.36 (s, 3H).

Preparation 25

2-Chloro-4-[7-(2-chloro-pyridin-4-yl)-benzo[b]thiophen-2-yl]-pyrimidine

In a 500 mL round bottom flask, cool a solution of 4-benzo[b]thiophen-7-yl-2-chloro-pyridine (13 g, 53.1 mmol) and triisopropylborate (20 g, 106 mmol) in THF (150 mL) to −70° under nitrogen. To the cooled solution, add lithium diisopropylamide (2 M in THF, 53 mL, 106 mmol) gradually over a period of 30 min. Stir the mixture continually for an additional 1 hour in the cooling bath. Gradually transfer the mixture into a refluxing solution of 2,4-dichloro-pyrimidine (12 g, 106 mmol), [1,1'-bis(diphenyl-phosphino)ferrocene]dichloropalladium(II), complex with dichloromethane (1:1) (2.2 g, 53 mmol) and sodium carbonate (35 mL, 3 M, 106 mmol) in THF (150 mL) over a period of 30 min. Reflux for an additional 1 hour. Cool the mixture to room temperature and dilute with 500 mL of chloroform/isopropanol (3/1) and 200 mL of water. Collect the resulting solid by filtration and reserve the chloroform/isopropanol/water mixture. Wash the solid with dichloromethane and dry it under vacuum. Separate the layers of the chloroform/isopropanol/water mixture. Wash the organic phase with water and saturated aqueous sodium chloride, dry over sodium sulfate and concentrate in vacuo to give a brown residue. Purify the residue by flash column chromatography (10% methanol in dichloromethane) to afford additional product. Combine the two portions to give the title compound (13 g, 68%) MS (ES) m/z 358 [M+1]⁺.

Prepare the following intermediates essentially according to the preparation of 2-chloro-4-[7-(2-chloro-pyridin-4-yl)-benzo[b]thiophen-2-yl]-pyrimidine using the appropriate starting material.

| Prep | Compound Name | Physical Data MS (ES) m/z [M + 1]+ | Comments |
|---|---|---|---|
| 26 | 2-Chloro-5-fluoro-4-(7-pyridin-4-yl-benzo[b]thiophen-2-yl)-pyrimidine | 342 | |
| 27 | 2-Chloro-5-methyl-4-(7-pyridin-4-yl-benzo[b]thiophen-2-yl)-pyrimidine | 338 | |
| 28 | 2-Chloro-5-fluoro-4-[7-(2-fluoro-5-methyl-pyridin-4-yl)-benzo[b]thiophen-2-yl]-pyrimidine | 374 | |
| 29 | 2-Chloro-4-[7-(2-fluoro-5-methyl-pyridin-4-yl)-benzo[b]thiophen-2-yl]-5-methyl-pyrimidine | 370 | |
| 30 | 2-Chloro-4-[7-(2-fluoro-5-methyl-pyridin-4-yl)-benzo[b]thiophen-2-yl]-pyrimidine | 356 | Additive: 2-(di-tert-butylphosphino)biphenyl |
| 31 | 2-Chloro-5-fluoro-4-[7-(3-methoxymethoxy-pyridin-4-yl)-benzo[b]thiophen-2-yl]-pyrimidine | 402 | |
| 32 | 2-Chloro-4-[7-(2-chloro-5-ethoxy-pyridin-4-yl)-benzo[b]thiophen-2-yl]-5-fluoro-pyrimidine | 420 | |
| 33 | {4-[2-(2-Chloro-pyrimidin-4-yl)-benzo[b]thiophen-7-yl]-6-fluoro-pyridin-3-yl}-carbamic acid tert-butyl ester | 457 | |

-continued

| Prep | Compound Name | Physical Data MS (ES) m/z [M + 1]+ | Comments |
|---|---|---|---|
| 34 | 4-(7-Bromo-benzo[b]thiophen-2-yl)-2-chloro-5-fluoro-pyrimidine | 343 | |
| 35 | 2,5-Dichloro-4-[7-(2-fluoro-5-methyl-pyridin-4-yl)-benzo[b]thiophen-2-yl]-pyrimidine | 390 | Additive: 2-(di-tert-butylphosphino)biphenyl |
| 36 | 4-(7-Bromo-benzo[b]thiophen-2-yl)-2-chloro-5-chloro-pyrimidine | 361 | |
| 37 | 4-(7-Bromo-benzo[b]thiophen-2-yl)-2-chloro-5-methyl-pyrimidine | 340 | GCMS (EI) M+ |
| 38 | 4-(7-Bromo-benzo[b]thiophen-2-yl)-2-chloro-pyrimidine | 327 | |

Preparation 39

4-[2-(2-Chloro-5-fluoro-pyrimidin-4-yl)-benzo[b]thiophen-7-yl]-pyridin-3-ol

Treat a solution of 2-chloro-5-fluoro-4-[7-(3-methoxymethoxy-pyridin-4-yl)-benzo[b]thiophen-2-yl]-pyrimidine (4 g, 10 mmol) in THF (10 mL) with 5 N HCl (3 mL). Stir the mixture at room temperature for 6 hours. Concentrate the reaction in vacuo and dilute with saturated aqueous sodium bicarbonate and dichloromethane. Separate the layers and filter each layer. Wash the solid from the organic phase with dichloromethane to give the title compound (300 mg) as a tan solid. Wash the solid from the aqueous layer with water and dry to give the title compound (300 mg) as a tan solid. Combine the solids to give the title compound (600 mg, 17%) as a tan solid. MS (ES) m/z 358 [M+1]+.

Preparation 40

2-Chloro-4-[7-(3-ethoxy-pyridin-4-yl)-benzo[b]thiophen-2-yl]-5-fluoro-pyrimidine Treat a solution of 4-[2-(2-chloro-5-fluoro-pyrimidin-4-yl)-benzo[b]thiophen-7-yl]-pyridin-3-ol (100 mg, 0.28 mmol) and cesium carbonate (100 mg, 0.28 mmol) in dimethylformamide (1 mL) with ethyl iodide (44 mg, 0.28 mmol). Stir the mixture at room temperature for 12 hours. Dilute the mixture with ethyl acetate and wash the solution with three portions of water, one portion of saturated aqueous sodium chloride, dry over sodium sulfate, filter, and concentrate in vacuo. Purify the crude product by column chromatography on 12 g silica gel eluting with a gradient of dichloromethane to ethyl acetate to give the title compound (48 mg, 45%) as a brown solid. MS (ES) m/z 386 [M+1]+.

Preparation 41

2-Chloro-5-fluoro-4-[7-(3-methoxy-pyridin-4-yl)-benzo[b]thiophen-2-yl]-pyrimidine Prepare the title compound essentially according to the preparation of 2-chloro-4-[7-(3-ethoxy-pyridin-4-yl)-benzo[b]thiophen-2-yl]-5-fluoro-pyrimidine using the appropriate starting material. MS (ES) m/z 372 [M+1]+

Preparation 42

1-{2-[4-(7-Bromo-benzo[b]thiophen-2-yl)-5-fluoro-pyrimidin-2-ylamino]-ethyl}-imidazolidin-2-one Combine 1-(2-aminoethyl)-2-imidazolone (100 g, 774 mmol) with 4-(7-bromo-benzo[b]thiophen-2-yl)-2-chloro-5-fluoro-pyrimidine (90 g, 262 mmol) in 1,4-dioxane (650 mL) and heat to 90° C. with stirring under nitrogen for 3 hours. Cool the reaction to room temperature. Filter and wash the solid with water (3×500 mL) and diethyl ether (500 mL). Vacuum-dry at 50° C. to give the title compound (59.2 g, 52%) as a yellow solid. MS (ES) m/z 436 [M+1]+.

Prepare the following intermediates essentially according to the preparation of 1-{2-[4-(7-bromo-benzo[b]thiophen-2-yl)-5-fluoro-pyrimidin-2-ylamino]-ethyl}-imidazolidin-2-one using the appropriate starting material.

| Prep | Compound name | Physical Data MS (ES) m/z [M + 1]+ |
|---|---|---|
| 43 | 1-{2-[4-(7-Bromo-benzo[b]thiophen-2-yl)-5-chloro-pyrimidin-2-ylamino]-ethyl}-imidazolidin-2-one | 454 |
| 44 | 1-{2-[4-(7-Bromo-benzo[b]thiophen-2-yl)-5-methyl-pyrimidin-2-ylamino]-ethyl}-imidazolidin-2-one | 432 |
| 45 | 1-{2-[4-(7-Bromo-benzo[b]thiophen-2-yl)-pyrimidin-2-ylamino]-ethyl}-imidazolidin-2-one | 420 |

Preparation 46

5-Bromomethyl-2-fluoro-4-iodo-pyridine

In a flask, combine 2-fluoro-4-iodo-picoline (10.0 g, 42.19 mmol), N-bromosuccinimide (9.76 g, 54.85 mmol), 2,2'-azobisisobutyronitrile (3.46 g, 21.10 mmol) and dry CCl$_4$ (100 mL). Heat at 70° C. under nitrogen for 16 hours. Cool to room temperature. Dilute with dichloromethane and wash with water and saturated aqueous sodium chloride. Separate the layers and dry the organic layer over magnesium sulfate. Concentrate in vacuo to give crude product. Purify by column chromatography (1% to 15% ethyl acetate in hexane) to afford the title compound (8.27 g, 62%). MS (EI) m/z 315M.

Preparation 47

1-(2-{5-Fluoro-4-[7-(4,4,5,5-tetramethyl-[1,3,2]dioxaborolan-2-yl)-benzo[b]thiophen-2-yl]-pyrimidin-2-ylamino}-ethyl)-imidazolidin-2-one Combine 1-{2-[4-(7-bromo-benzo[b]thiophen-2-yl)-5-fluoro-pyrimidin-2-ylamino]-ethyl}-imidazolidin-2-one (5.5 g, 12.6 mmol), bis(pinacolato)diboron (3.84 g, 15.3 mmol), (1,1'-bis(diphenylphosphino)-ferrocene)dichloropalladium (II) (1.0 g, 1.3 mmol), potassium acetate (2.5 g, 25 mmol) in DMSO (80 mL) in a flask. Bubble nitrogen through the mixture for 10 min. Seal the flask and put it into an oil bath to heat at 85° C. overnight. Dilute the mixture with chloroform/isopropyl alcohol (3/1). Wash the solution with saturated aqueous sodium chloride. Dry it over sodium sulfate. Concentrate the solution in vacuo to a dark residue. Purify the residue by column chromatography (hexane→20% ethyl acetate in hexane→10% methanol in dichloromethane) to afford the product as a brown solid (5 g, 82%). MS (ES) m/z 484 [M+1]$^+$.

Preparation 48

(6-Fluoro-4-iodo-pyridin-3-yl)-methanol

Combine 5-bromomethyl-2-fluoro-4-iodo-pyridine (0.9 g, 2.85 mmol), nitromethane (15 mL, 278 mmol), silver tetrafluoroborate (721 mg, 3.7 mmol), and dimethylformamide (5 mL) in a round bottom flask. Stir the mixture overnight at room temperature. Add sodium carbonate (1.81 g, 17.1 mmol) and methanol (10 mL) into the mixture. Stir at room temperature for another 4 hours. Dilute the reaction mixture with chloroform, and wash with water and saturated aqueous sodium chloride. Separate the organic layer from the aqueous layer and dry over MgSO$_4$. After filtration, evaporate the organic solvent in vacuo to give the crude product. Purify the crude with flash column chromatography (eluted with 10% methanol in dichloromethane) to give the desired product (0.6 g, 83%). MS (ES) m/z 254 [M+1]$^+$.

Preparation 49

2-Fluoro-5-fluoromethyl-4-iodo-pyridine

Add diethylaminosulfur trifluoride (892 mg, 4 mmol) drop-wise to a solution of (6-fluoro-4-iodo-pyridin-3-yl)-methanol in dichloromethane (25 mL) in a round bottom flask under nitrogen, and then add ethanol (0.3 mL) at 0-5° C. Stir the mixture for 3 hours. Pour the reaction mixture into saturated sodium bicarbonate solution. Abstract the product into chloroform, and wash with water and saturated aqueous sodium chloride. Separate the organic layer from the aqueous layer and dry over MgSO$_4$. After filtration, evaporate the organic solvent in vacuo to give a crude product. Purify the crude with flash column chromatography (10% methanol in dichloromethane) to give the title compound (0.32 g, 53%). MS (ES) m/z 256 [M+1]$^+$.

EXAMPLES

Example 1

1-(2-{4-[7-(2-Chloro-pyridin-4-yl)-benzo[b]thiophen-2-yl]pyrimidin-2-ylamino}ethyl)imidazolidin-2-one

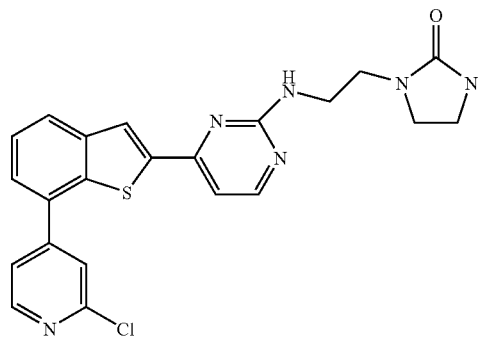

Combine 2-chloro-4-[7-(2-chloro-pyridin-4-yl)-benzo[b]thiophen-2-yl]-pyrimidine (9 g, 25.1 mmol) and 2-(aminoethyl)-1,3-dihydro-imidazol-one (6.4 g, 50.2 mmol) in n-butanol (200 mL) in a pressure vessel. Heat the mixture in an oil bath at 120° C. for 5 hours. Dilute the mixture with chloroform/isopropanol (3/1). Wash the solution with saturated aqueous sodium chloride. Dry it over sodium sulfate. Concentrate the solution in vacuo to a dark residue. Purify by column chromatography (dichloromethane to 10% methanol in dichloromethane) to afford the title compound (9 g, 93%) as a yellow solid. MS (ES) m/z 451 [M+1]$^+$.

Prepare the following examples essentially according to the preparation of 1-(2-{4-[7-(2-chloro-pyridin-4-yl)-benzo[b]thiophen-2-yl]pyrimidin-2-ylamino}-ethyl)-imidazolidin-2-one using the appropriate starting material.

| Ex | Compound name | Structure | Physical Data MS (ES) m/z [M + 1]$^+$ | Comments |
|---|---|---|---|---|
| 2 | 1-(2-{5-Fluoro-4-[7-(2-fluoro-5-methylpyridin-4-yl)-benzo[b]thiophen-2-yl]-pyrimidin-2-ylamino}ethyl)imidazolidin-2-one | 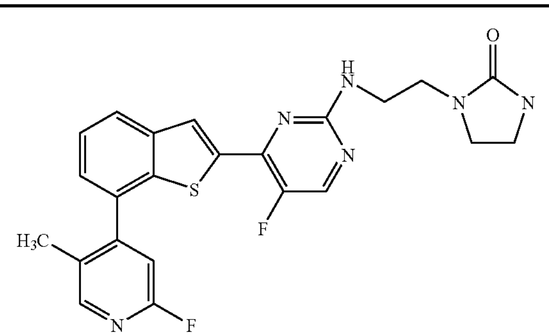 | 467 | Microwave, 1,4-dioxane-NMP 120° C. |

-continued

| Ex | Compound name | Structure | Physical Data MS (ES) m/z [M + 1]+ | Comments |
|---|---|---|---|---|
| 3 | 1-(2-{4-[7-(2-Fluoro-5-methylpyridin-4-yl)-benzo[b]thiophen-2-yl]-5-methylpyrimidin-2-ylamino}ethyl)imidazolidin-2-one | 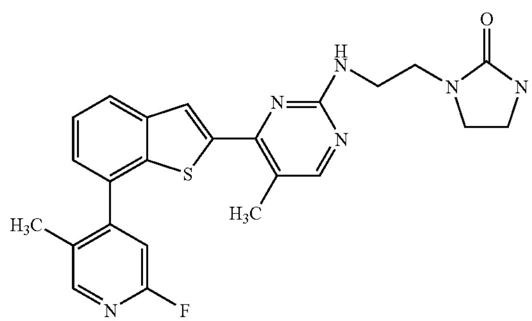 | 463 | Microwave, 1,4-dioxane-NMP 120° C. |
| 4 | 1-(2-{4-[7-(2-Fluoro-5-methylpyridin-4-yl)-benzo[b]thiophen-2-yl]pyrimidin-2-ylamino}-ethyl)imidazolidin-2-one | 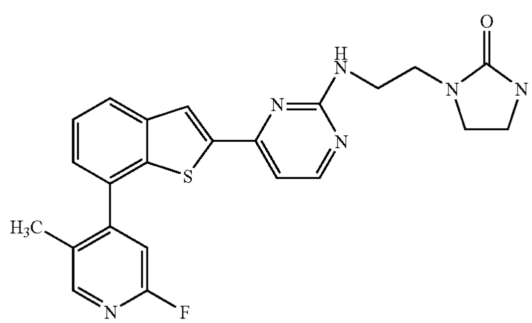 | 449 | Additive: Triethyl amine-3 equivalents |
| 5 | 1-{2-[5-Methyl-4-(7-pyridin-4-yl-benzo[b]thiophen-2-yl)pyrimidin-2-ylamino]-ethyl}imidazolidin-2-one | 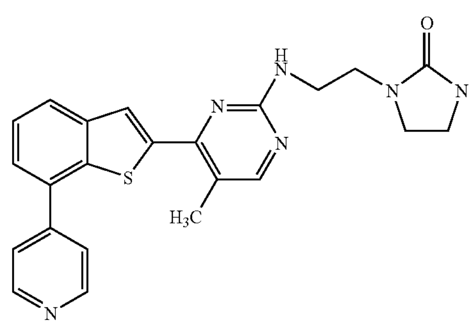 | 431 | Microwave, NMP 120° C. |
| 6 | 1-(2-{5-Chloro-4-[7-(2-fluoro-5-methylpyridin-4-yl)benzo[b]thiophen-2-yl]-pyrimidin-2-ylamino}ethyl)imidazolidin-2-one | 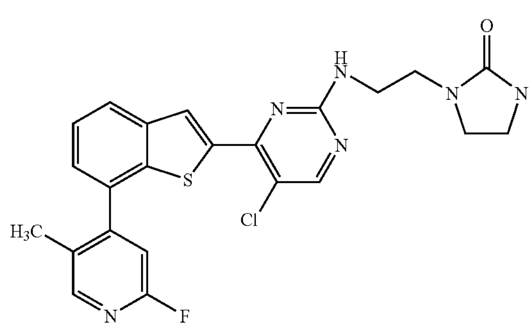 | 483 | Additive: Triethyl amine-3 equivalents |

-continued

| Ex | Compound name | Structure | Physical Data MS (ES) m/z [M + 1]+ | Comments |
|---|---|---|---|---|
| 7 | 1-{2-[5-Fluoro-4-(7-pyridin-4-yl-benzo[b]thiophen-2-yl)pyrimidin-2-ylamino]-ethyl}imidazolidin-2-one | 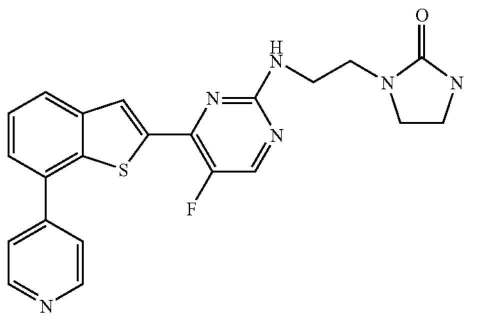 | 435 | Microwave, NMP 120° C. |
| 8 | 1-(2-{4-[7-(3-Ethoxypyridin-4-yl)-benzo[b]thiophen-2-yl]-5-fluoropyrimidin-2-ylamino}ethyl)imidazolidin-2-one | 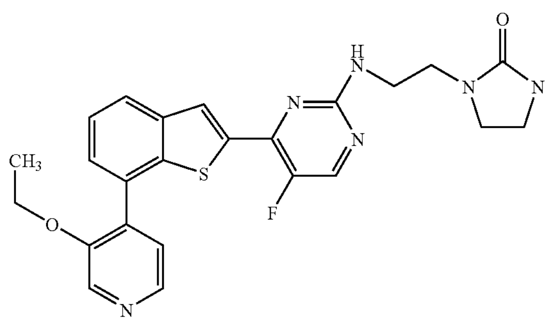 | 479 | |
| 9 | 1-(2-(5-Fluoro-4-(7-(3-hydroxypyridin-4-yl)benzo[b]thiophen-2-yl)pyrimidin-2-ylamino)ethyl)imidazolidin-2-one | 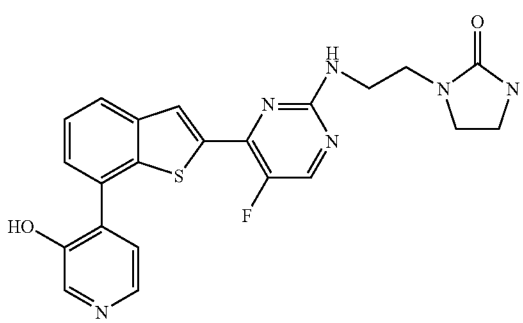 | 451 | |
| 10 | 1-(2-{4-[7-(2-Chloro-5-ethoxypyridin-4-yl)-benzo[b]thiophen-2-yl]-5-fluoropyrimidin-2-ylamino}-ethyl)imidazolidin-2-one | 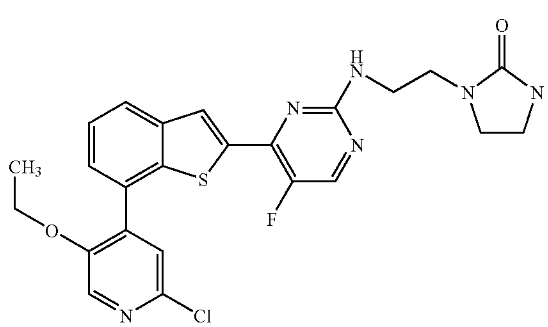 | 513 | |

-continued

| Ex | Compound name | Structure | Physical Data MS (ES) m/z [M + 1]+ | Comments |
|----|---|---|---|---|
| 11 | 1-(2-{5-Fluoro-4-[7-(3-methoxypyridin-4-yl)-benzo[b]thiophen-2-yl]pyrimidin-2-ylamino}-ethyl)imidazolidin-2-one | 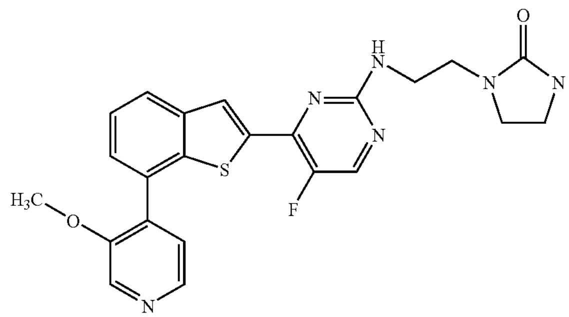 | 465 | |

Example 12

1-(2-(5-Chloro-4-(7-(pyridin-4-yl)benzo[b]thiophen-2-yl)pyrimidin-2-ylamino)ethyl)imidazolidin-2-one

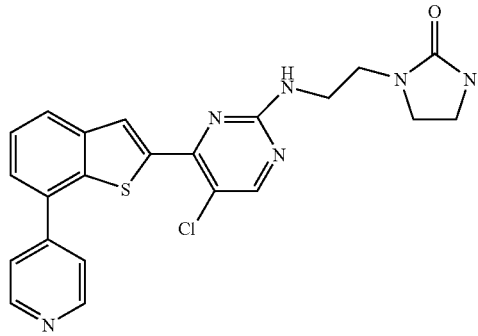

Combine 1-{2-[4-(7-bromo-benzo[b]thiophen-2-yl)-5-chloro-pyrimidin-2-ylamino]-ethyl}-imidazolidin-2-one (81.6 mg, 0.18 mmol), pyridine-4-boronic acid (36.8 mg, 0.3 mmol), and sodium bicarbonate (18.1 mg, 0.2 mmol) in a mixture of water (1 mL) and DMSO (1 mL). Add tetrakis (triphenylphosphine)palladium(0) (10.4 mg, 0.009 mmol). Irradiate the mixture at 150° C. for 15 min with magnetic stirring. Pour the crude reaction mixture onto a strong cation exchange (SCX) (10 g) column. Elute the desired product with 2 N ammonia in methanol (40 mL) and concentrate under reduced pressure. Purify by reverse phase chromatography (30 to 90% gradient at 80 mL/min for 11 min on a 30×100 mm, 5 mm, $C_{18}$ MS Xterra® column, Solvent A: water with 0.01 M ammonium bicarbonate, Solvent B: acetonitrile) to afford the title compound (20.4 mg, 25.1%). MS (ES) m/z 451 [M+1]+.

Example 13

1-(2-{5-Chloro-4-[7-(5-chloro-2-fluoropyridin-4-yl)-benzo[b]thiophen-2-yl]pyrimidin-2-ylamino}ethyl)imidazolidin-2-one

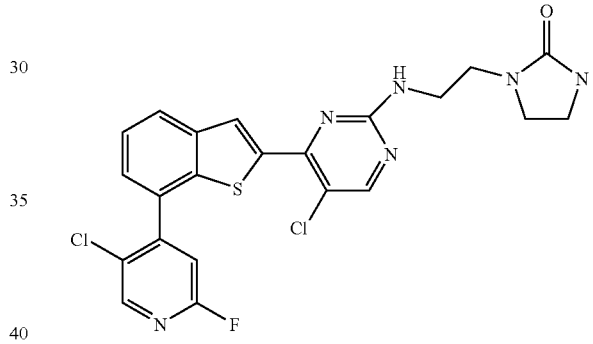

In a microwave vial, combine 1-{2-[4-(7-bromo-benzo[b]thiophen-2-yl)-5-chloro-pyrimidin-2-ylamino]-ethyl}-imidazolidin-2-one (500 mg, 1.1 mmol), 5-chloro-2-fluoropyridine-4-boronic acid (578 mg, 3.3 mmol), [1,1'-bis(diphenylphosphino) ferrocene]dichloropalladium(II), complex with dichloromethane (1:1) (90 mg, 0.11 mmol), 2-(di-tert-butylphosphino)biphenyl (20 mg, 0.066 mmol) and sodium carbonate (350 mg, 3.3 mmol) in THF (3 mL) and water (1.5 mL). Bubble nitrogen through the mixture for 5 min. Heat the mixture to 100° C. for 10 min. Concentrate the organic layer to dryness in vacuo. Slurry the resulting solid into dichloromethane/methanol and purify by column chromatography (1% 2 N ammonia/methanol solution in dichloromethane to 10% 2 N ammonia/methanol solution in dichloromethane) to afford the title compound. For further purification, dissolve the product in DMSO and purify by reverse phase column chromatography (50% acetonitrile in water (with 0.03% HCl) to 95% acetonitrile in water (with 0.03% HCl) to afford the title compound (146 mg, 26%). MS (ES) m/z 503 [M+1]+.

Prepare the following examples essentially according to the preparation of 1-(2-{5-chloro-4-[7-(5-chloro-2-fluoropyridin-4-yl)benzo[b]thiophen-2-yl]-pyrimidin-2-ylamino}ethyl)imidazolidin-2-one using the appropriate starting material.

| Ex | Compound Name | Structure | Physical Data MS (ES) m/z [M + 1]+ | Comments |
|---|---|---|---|---|
| 14 | 1-(2-{4-[7-(2-Chloro-pyridin-4-yl)-benzo[b]thiophen-2-yl]-5-fluoropyrimidin-2-ylamino}ethyl)imidazolidin-2-one | 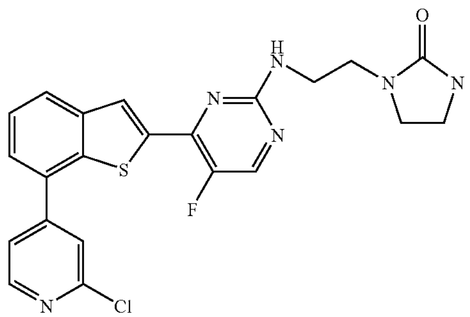 | 469 | |
| 15 | 1-(2-{5-Chloro-4-[7-(2-chloro-pyridin-4-yl)benzo[b]thiophen-2-yl]pyrimidin-2-ylamino}ethyl)imidazolidin-2-one | 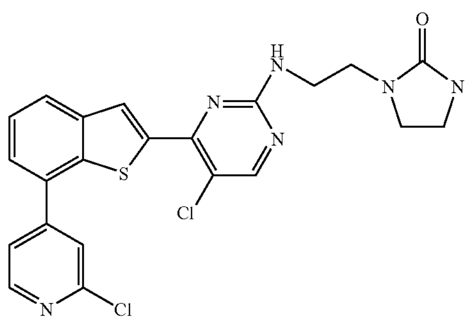 | 486 | |
| 16 | 1-(2-{4-[7-(5-Chloro-2-fluoro-pyridin-4-yl)-benzo[b]thiophen-2-yl]-5-fluoropyrimidin-2-ylamino}ethyl)imidazolidin-2-one | 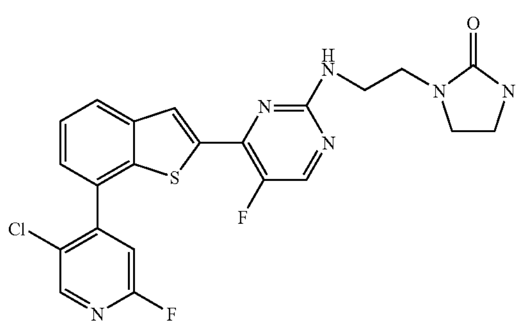 | 487 | Purify by reverse phase, CH$_3$CN and water |
| 17 | 1-(2-{4-[7-(2-Chloro-5-fluoropyridin-4-yl)-benzo[b]thiophen-2-yl]-5-fluoropyrimidin-2-ylamino}-ethyl)imidazolidin-2-one | 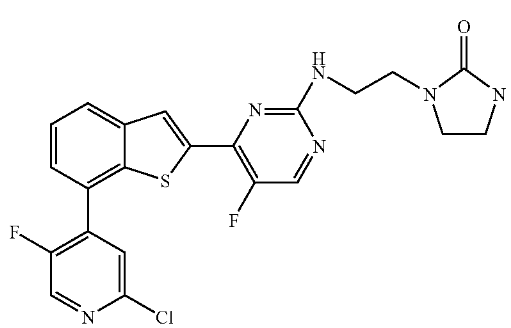 | 487 | Purify by reverse phase, CH$_3$CN and water |

-continued

| Ex | Compound Name | Structure | Physical Data MS (ES) m/z [M + 1]+ | Comments |
|---|---|---|---|---|
| 18 | 1-(2-{4-[7-(3-Chloro-pyridin-4-yl)-benzo[b]thiophen-2-yl]-5-fluoropyrimidin-2-ylamino}ethyl)imidazolidin-2-one | 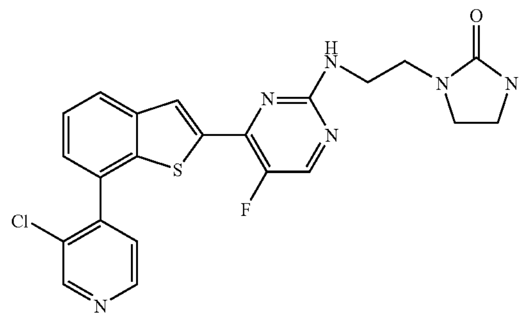 | 469 | Purify by reverse phase, $CH_3CN$ and water |
| 19 | 1-(2-{5-Fluoro-4-[7-(3-methylpyridin-4-yl)-benzo[b]thiophen-2-yl]pyrimidin-2-ylamino}ethyl)imidazolidin-2-one | 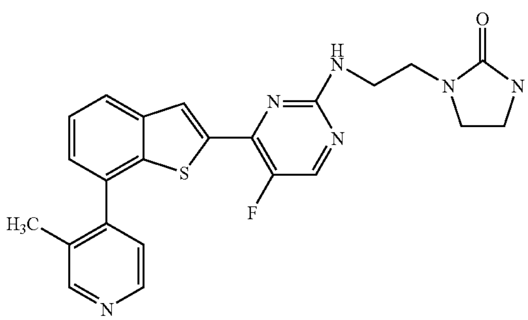 | 449 | Purify on reverse phase, $CH_3CN$ and water |
| 20 | 1-(2-{4-[7-(5-Chloro-2-fluoropyridin-4-yl)-benzo[b]thiophen-2-yl]-5-methylpyrimidin-2-ylamino}ethyl)imidazolidin-2-one | 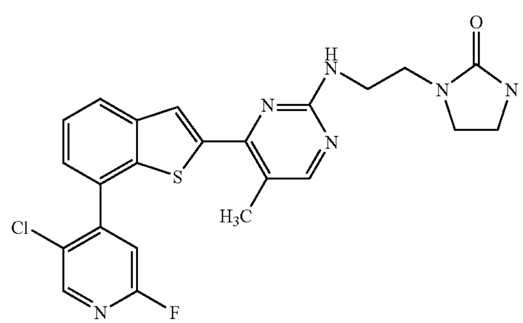 | 483 | Purify on reverse phase, $CH_3CN$ and water |
| 21 | 1-(2-{4-[7-(2,5-Dichloropyridin-4-yl)-benzo[b]thiophen-2-yl]-5-fluoropyrimidin-2-ylamino}ethyl)imidazolidin-2-one | 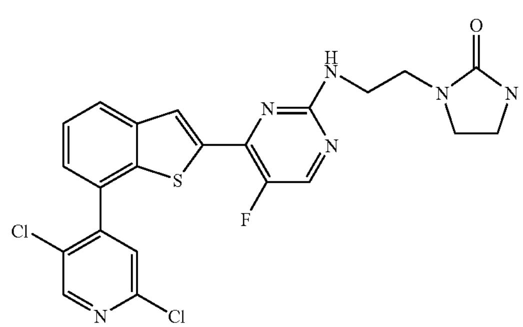 | 503 | |

-continued

| Ex | Compound Name | Structure | Physical Data MS (ES) m/z [M + 1]+ | Comments |
|----|---------------|-----------|------------------------------------|----------|
| 22 | 1-(2-{5-Fluoro-4-[7-(2-fluoropyridin-4-yl)-benzo[b]thiophen-2-yl]pyrimidin-2-ylamino}ethyl)imidazolidin-2-one | 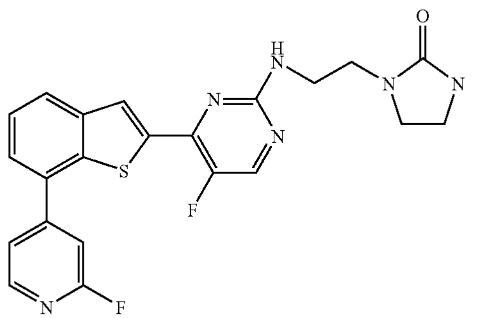 | 453 | |
| 23 | 1-(2-{4-[7-(5-Chloro-2-fluoro-pyridin-4-yl)-benzo[b]thiophen-2-yl]pyrimidin-2-ylamino}ethyl)imidazolidin-2-one | 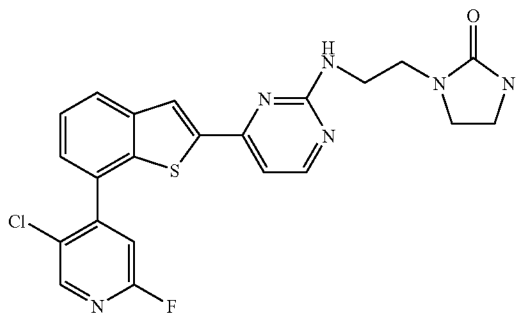 | 469 | |

Example 24

4-(2-(2-(2-(2-Oxoimidazolidin-1-yl)ethylamino)pyrimidin-4-yl)benzo[b]thiophen-7-yl)picolinonitrile

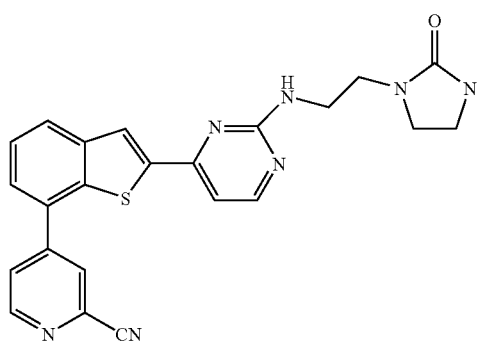

Combine 1-(2-{4-[7-(2-chloro-pyridin-4-yl)-benzo[b]thiophen-2-yl]-pyrimidin-2-ylamino}-ethyl)-imidazolidin-2-one (100 mg, 0.22 mmol), zinc cyanide (51 mg, 0.44 mmol), tris(dibenzylideneacetone)dipalladium(0) (10 mg, 0.01 mmol), 1,1'-bis(diphenylphosphino)-ferrocene (6 mg, 0.01 mmol) in DMSO (6 mL). Heat the mixture at 100° C. for 4 hours. Cool the mixture to room temperature and load onto a silica column. Elute the column with 10% methanol in dichloromethane to afford the title compound (0.7 g, 72%) as yellow oil. MS (ES) m/z 442 [M+1]+.

Example 25

1-(2-{4-[7-(3-Amino-pyridin-4-yl)benzo[b]thiophen-2-yl]-5-fluoropyrimidin-2-ylamino}ethyl)imidazolidin-2-one

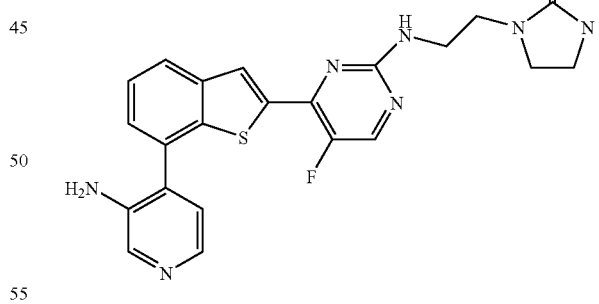

Combine N-{4-[2-(2-chloro-5-fluoro-pyrimidin-4-yl)-benzo[b]thiophen-7-yl]-pyridin-3-yl}-2,2-dimethyl-propionamide (330 mg, 0.75 mmol), 2-(amino-ethyl)-1,3-dihydro-imidazolone (386 mg, 3.0 mmol), and 1,4-dioxane (6 mL) in a capped vial and heat at 85° C. for 4 hours. Concentrate in vacuo. Dilute the mixture with dichloromethane and water. Wash the organic solution with water. Dry the organic solution over sodium sulfate. Filter and concentrate the solution in vacuo to a dark residue. Purify by column chromatography (dichloromethane to 7% methanol in dichloromethane) to afford N-[4-(2-{5-fluoro-2-[2-(2-oxo-imidazolidin-1-yl)- ethylamino]-pyrimidin-4-yl}-benzo[b]thiophen-7-yl)-pyridin-3-yl]-2,2-dimethyl-propionamide.

Transfer the amide intermediate to a 40 mL septum capped vial. Add a magnetic stir bar and charge water (20 mL) and concentrated $H_2SO_4$ (5 mL) to the vial. Warm the vial to 90° C. in an oil bath for 5 hours. Cool the reaction to room temperature and pass through an SCX (10 g) column. Elute with water/methanol 1:1, then 100% methanol, then 1:1 dichloromethane/methanol, and finally elute the product off with 10% 2 M ammonia in methanol/90% dichloromethane.

Concentrate in vacuo. Chromatograph on silica (80 g) eluting with gradient of 0% to 10% 2 M ammonia/methanol solution in dichloromethane. Dry in vacuum oven at 42° C. for 2 hours to give the title compound (192.6 mg, 48%) as a gold solid. MS (ES) m/z 450 [M+1]$^+$.

Prepare the following examples essentially according to the preparation of 1-(2-{4-[7-(3-amino-pyridin-4-yl)benzo[b]thiophen-2-yl]-5-fluoropyrimidin-2-ylamino}-ethyl)imidazolidin-2-one using the appropriate starting material.

| Ex | Compound name | Structure | Physical Data MS (ES) m/z [M + 1]$^+$ |
|---|---|---|---|
| 26 | 1-(2-{4-[7-(3-Methylamino-pyridin-4-yl)benzo[b]thiophen-2-yl]pyrimidin-2-ylamino}ethyl)imidazolidin-2-one | 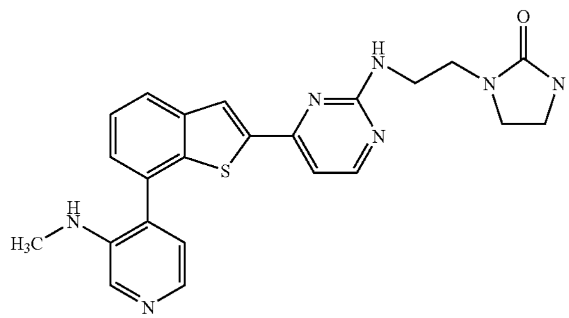 | 446 |
| 27 | 1-(2-{4-[7-(3-Amino-pyridin-4-yl)benzo[b]thiophen-2-yl]-5-methylpyrimidin-2-ylamino}ethyl)imidazolidin-2-one | 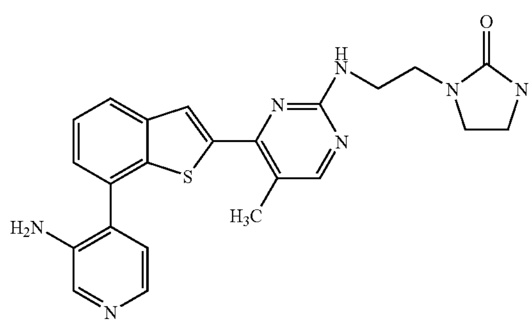 | 446 |
| 28 | 1-(2-{4-[7-(3-Amino-pyridin-4-yl)benzo[b]thiophen-2-yl]-pyrimidin-2-ylamino}ethyl)imidazolidin-2-one | 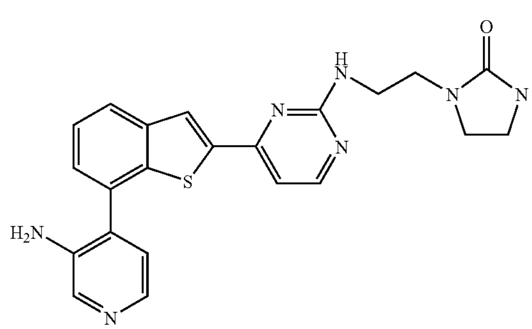 | 432 |

Example 29

1-(2-{4-[7-(5-Amino-2-fluoropyridin-4-yl)benzo[b]thiophen-2-yl]pyrimidin-2-ylamino}ethyl)imidazolidin-2-one

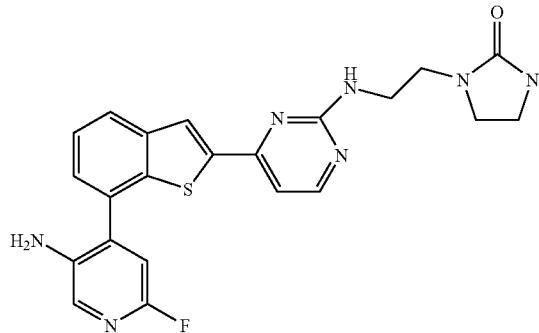

Combine {4-[2-(2-chloro-pyrimidin-4-yl)-benzo[b]thiophen-7-yl]-6-fluoro-pyridin-3-yl}-carbamic acid tert-butyl ester (813 mg, 1.77 mmol), 2-(amino-ethyl)-1,3-dihydro-imidazol-one (919 mg, 7.11 mmol), and 1,4-dioxane (22 mL) in a capped vial and heat at 70° C. for 15 hours. Concentrate in vacuo. Dilute the mixture with dichloromethane and water. Wash the organic solution with water. Dry the organic solution over sodium sulfate. Filter and concentrate the solution in vacuo to a dark residue. Purify by column chromatography (dichloromethane to ethyl acetate) to afford [6-fluoro-4-(2-{2-[2-(2-oxo-imidazolidin-1-yl)-ethylamino]-pyrimidin-4-yl}-benzo[b]thiophen-7-yl)-pyridin-3-yl]-carbamic acid tert-butyl ester.

Dissolve the [6-fluoro-4-(2-{2-[2-(2-oxo-imidazolidin-1-yl)-ethylamino]-pyrimidin-4-yl}-benzo[b]thiophen-7-yl)-pyridin-3-yl]-carbamic acid tert-butyl ester into dichloromethane and adsorb onto silica gel (10 g) via concentration in vacuo. Dry under high vacuum for 24 hours. Place silica gel into a round bottom flask and heat in a temperature controlled oil bath to 98-99° C. while under high vacuum for 2 hours. Cool to room temperature. Extract product from silica gel with 10% 7 N ammonia in methanol/90% dichloromethane. Concentrate in vacuo. Chromatograph on silica eluting with a gradient of 100% dichloromethane to 7% 2 N ammonia in methanol/93% dichloromethane to afford the title compound (65.2 mg, 8.2%). MS (ES) m/z 450 [M+1]$^+$.

Example 30

1-(2-{4-[7-(3-Amino-2-fluoropyridin-4-yl)benzo[b]thiophen-2-yl]pyrimidin-2-ylamino}ethyl)imidazolidin-2-one

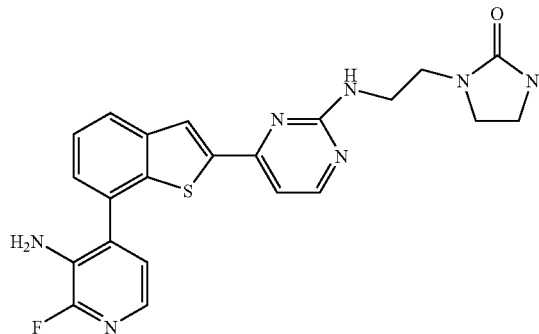

Prepare the title compound essentially according to the preparation of 1-(2-{4-[7-(5-amino-2-fluoro-pyridin-4-yl)-benzo[b]thiophen-2-yl]-pyrimidin-2-ylamino}-ethyl)-imidazolidin-2-one using the appropriate starting material. MS (ES) m/z 450 [M+1]$^+$.

Example 31

1-(2-{5-Fluoro-4-[7-(2-fluoro-5-hydroxymethyl-pyridin-4-yl)benzo[b]thiophen-2-yl]pyrimidin-2-ylamino}ethyl)imidazolidin-2-one

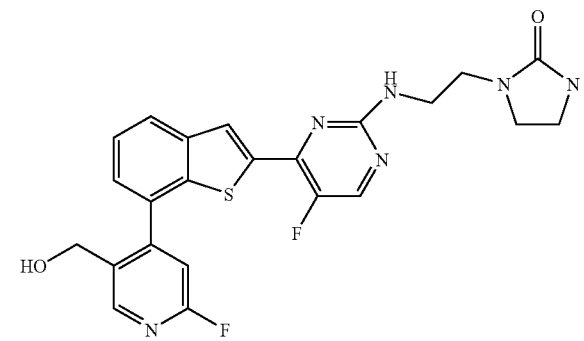

Combine 1-(2-{5-fluoro-4-[7-(4,4,5,5-tetramethyl-[1,3,2]dioxaborolan-2-yl)-benzo[b]thiophen-2-yl]-pyrimidin-2-ylamino}-ethyl)-imidazolidin-2-one (120 mg, 0.25 mmol), (6-fluoro-4-iodo-pyridin-3-yl)-methanol (100 mg; 0.32 mmol), (1,1'-bis(di-phenylphosphino)ferrocene)palladium(II) chloride (10.14 mg; 0.01 mmol), 2-(di-tert-butylphosphino)biphenyl (2 mg, 0.01 mmol) and sodium carbonate (2 M, 0.2 mL, 0.4 mmol) in 5 mL of dioxane in a pressure tube. Heat the mixture at 100° C. overnight in oil bath. Cool the mixture down to room temperature, dilute it with chloroform-isopropyl alcohol (3/1). Wash the organic phase with saturated aqueous sodium chloride, dry it over sodium sulfate and concentrate it to an oily residue. Purify the crude by flash column chromatography (10% methanol in dichloromethane) to afford the title compound (25 mg, 21%). MS (ES) m/z 483 [M+1]$^+$.

Example 32

1-(2-{5-Fluoro-4-[7-(2-fluoro-5-(fluoromethyl)pyridin-4-yl)benzo[b]thiophen-2-yl]pyrimidin-2-ylamino}ethyl)imidazolidin-2-one

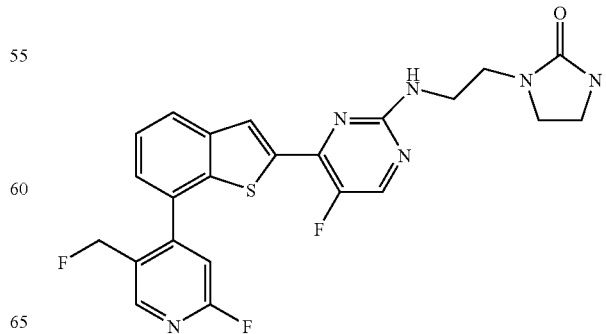

Combine 1-(2-{5-fluoro-4-[7-(4,4,5,5-tetramethyl-[1,3,2]dioxaborolan-2-yl)-benzo[b]thiophen-2-yl]-pyrimidin-2-ylamino}-ethyl)-imidazolidin-2-one (120 mg, 248.26 µmol), 2-fluoro-5-fluoromethyl-4-iodo-pyridine (100 mg, 392.15 µmol) tris(dibenzylideneacetone)dipalladium (0) (11.37 mg, 12.41 µmol) tricyclohexylphosphine (2.09 mg, 7.45 µmol), potassium phosphate (105.39 mg, 496.51 µmol) in 5 mL of dioxane in a sealed pressure tube. Heat the mixture at 100° C. for 3 hours in the oil bath. LC-MS shows a peak at 485. Cool the reaction mixture down to room temperature and dilute it with chloroform-isopropyl alcohol (3/1). Wash the organic solution with saturated aqueous sodium chloride, dry it over sodium sulfate and concentrate it to crude. Purify the crude by flash chromatography (10% methanol in dichloromethane) to give the target product (70 mg, 58.2%). MS (ES) m/z 485 [M+1]$^+$.

Assays

Plk1 has been shown to be over expressed in many human tumors, such as non-small cell lung, oropharyngeal, oesophageal, gastric, melanoma, breast, ovarian, endometrial, colorectal, glioblastoma, papillary, pancreatic, prostate, hepatoblastoma and non-Hodgkin lymphoma cancers. Furthermore, Plk1 expression has prognostic significance in non-small cell lung, oropharyngeal, oesophageal, melanoma, colorectal, hepatoblastoma and non-Hodgkin lymphoma cancers (Strebhardt, K. and A. Ullrich (2006). *Nature Reviews Cancer* 6(4): 321-30). Plk1 phosphorylated substrates regulate progression of mitosis by coordinating centrosome maturation, entry into mitosis, sister chromatid separation and cytokinesis (Eckerdt and Strebhardt 2006; Strebhardt and Ullrich 2006; van de Weerdt, B. C. and R. H. Medema (2006). *Cell Cycle* 5(8): 853-64). Inhibiting Plk1 function using antibody injection, expression of a dominant negative Plk1, and antisense mRNA reduction produces monopole spindles and anaphase arrest leading to mitotic cell death in tumor cell lines but reversible G2 arrest in normal non-transformed primary cell lines.

Additionally, it has been reported that Plk may be useful in the treatment of rhabdoid tumors, (Morozov A., et al., Clinical Cancer Research. 13(16):4721-30, (Aug. 15, 2007).

BI-2536 has demonstrated activity in preclinical models using HCT116, A549 and NCIH460 murine xenografts (Baum, A., P. Garin-Chesa, et al. (2006). #C191 *In vivo activity of BI 2536, a potent and selective inhibitor of the mitotic kinase PLK1, in a range of cancer xenografts*. AACR-NCI-EORTC International Conference on "Molecular Targets and Cancer Therapeutics", Philadelphia, Pa.).

The results of the following assays demonstrate evidence that the compounds of the present invention are useful as anticancer agents.

Expression and Purification of Plk1

Human Plk1 cDNA, which may be obtained from a number of sources, such as Incyte (accession number: NM_005030), may be directly linked at one of its termini with a polynucleotide sequence expressing a His$_6$ tag, such as the C-terminal FLAG-His$_6$ tag, and inserted into an appropriate expression vector, such as a pFastBac™ vector (Invitrogen) and transfected into an appropriate system, such as baculovirus similar to what has been reported by Yue-Wei Qian, et al., Science 282, 1701 (1998) for xPlkk1. If a viral expression system is used, then the virus (e.g., baculovirus bearing a Plk1-Flag-His$_6$ tag polynucleotide construct) is infected into a culture of a suitable host cell, such as Sf9 cells. When sufficient amounts of the Plk1-Flag-His$_6$ tag fusion protein have been expressed, for example, at about 46 hours after infection, the culture should be treated with okadaic acid (0.1 µM) for a sufficient period of time (e.g., 3 hours). The Plk1-Flag-His$_6$ tag fusion is purified from cell pellets using a metal affinity resin, such as TALON™ (Clontech, Catalog # 635503) using methods well known in the art. Purified Plk1-Flag-His$_6$ tag fusion is stored in a suitable medium, such as 10 mM HEPES, 150 mM NaCl, 0.01% TRITON® X-100, 1 mM dithiothreitol (DTT), 10% glycerol, pH 7.5, at −80° C. in small aliquots until use. The identity of the purified Plk1-Flag-His$_6$ tag fusion protein is confirmed by MALDI (Matrix-Assisted Laser Desorption/Ionization).

Expression and Purification of GST-Cdc25C(1-206)

Human Cdc25C cDNA, which may be obtained from any appropriate source, such as Incyte (accession number: AY497-474), may be expressed in any convenient expression system, after which purification is effected by well known methods similar to that described by Bin Ouyang et al, Oncogene, 18, 6029-6036 (1999). One convenient system involves overnight growth at 18° C. of *E. coli* BL21 transformed with the pGEX-2T vector (Amersham) into which the cDNA for human Cds25C has been engineered for induced expression using 1 mM isopropyl-beta-D-thiogalactopyranoside. The expressed GST-Cdc25C(1-206), the substrate for Plk1, may be purified by GLUTATHIONE SEPHAROSE® 4B and stored in an appropriate solution, such as 10 mM HEPES, 100 mM NaCl, pH 7.5 in small aliquots at −80° C.

Plk1 Inhibition Assay

Plk1 kinase reactions contain Plk1-Flag-His$_6$ tag fusion enzyme (0.2 ng/µL) in a buffer containing 50 mM HEPES, pH 7.3, 1.0 mM dithiothreitol, 5.0 µM ATP, 10 mM MgCl$_2$, 0.01% TRITON® X-100, 0.4 µCi $^{33}$P-ATP, and 0.06 µg/µL GST-Cdc25c (1-206) peptide. Compounds are provided as 10 mM stocks in DMSO. Compounds are serially diluted 1:3 in 20% DMSO to create a 10-point concentration-response curve and subsequently are diluted 1:5 (20 µM to 0.001 µM final in 4% final DMSO concentration) in the reaction mixture to determine compound activity. The reaction is carried out at room temperature for 60 min and then quenched by adding 60 µL of 10.0% H$_3$PO$_4$. The reaction mixture (85 µL) is transferred to a 96 well phosphocellulose filter plate pre-wetted with 30 µL of 10.0% H$_3$PO$_4$, incubated at room temperature for 20-30 min and then washed 3× with 0.5% H$_3$PO$_4$. Wells are dried before addition of 40 µL of MicroScint™20 (Packard) and then counted on a Wallac MICROBETA® Jet. The percentage inhibition values from the 10-point concentration response data are subsequently analyzed, for example, using ACTIVITY BASE™ software (IDBS), using a 4-parameter logistic equation. Absolute IC$_{50}$ values are calculated from the resulting curve fit. All exemplified compounds have an IC$_{50}$ less than 100 nM with a Minimum Significant Ratio (MSR) of 3.6. For example, Example 13 has an IC$_{50}$ of about 23 nM.

pHH3(S10), Mitotic Cells, and DNA Content Assays

HeLa Cells from the American Type Culture Collection (ATCC) are plated at 200 cells/well in 96 well Beckman Dickinson BIOCOAT™ plates, and are incubated in MEM (Minimum Essential Medium, e.g., GIBCO, catalog #11095) with 10% FBS (Fetal Bovine Serum) in 37° C., 5% CO$_2$ for 24 hours. Cells are treated by adding compound (in 0.25%

DMSO) to the medium, dosing at 10 points across the range 0.5 μM to 0.0098 μM. After 23 hours exposure to the compounds, cells are fixed, for example with the PREFER™ fixative [Anatech LTD., Catalog #414] for 30 min then are permeabilized with 0.1% TRITON® X100 in phosphate buffered saline (PBS) solution for 15 min. Cells are washed 3 times with PBS then digested with 50 μg/mL RNAse. Primary antibody, phosphohistone H3 (Upstate Cat#06-570), is added at 1:500 in PBS with 1% bovine serum albumin (BSA) to the cells over night at 4° C. After 3 PBS washes, cells are incubated with Alexa488 labeled secondary antibody (Invitrogen cat #A11008) for 1 hour at room temperature. Again they are washed 3 times with PBS, and then 15 μM propidium iodide (Molecular Probes cat #P3566) is added for 30 min to stain nuclei. Fluorescence Plates are scanned with ACUMEN EXPLORER™ [Laser-scanning fluorescence microplate cytometer (comprising of 488 nm argon ion laser excitation and multiple photomultiplier tube detection), manufactured by TTP LABTECH LTD] to measure phosphohistone H3, DNA content and mitotic cells as measured by DNA condensation. Image analyses are based on cellular fluorescent signals for identifying cells in different subpopulations. pHH3 (S10) positive cells are identified by mean intensity at 500-530 nm above the threshold. Total intensity at 655-705 nm from propidium iodide/DNA is used to identify individual cells (cells with DNA content from 2N to 4N) and subpopulations in cell cycle (2N cells, 4N cells). Peak intensity at 575-640 nm is used to identify DNA condensation that is used as the marker to identify mitotic cells among 4N cells. Assay outputs are percentage of each identified subpopulations, % pHH3, % 2N, % 4N, % mitotic and total cell number. The $EC_{50}$ is determined by curve fitting to a four parameter logistic for each output using ACTIVITY BASE™. The resulting $EC_{50}$s for PHH3(s10), DNA content, and mitotic have an MSR of 2.6, 2.4 and 2.5, respectively. For example, Example 13 has a pHH3(s10) $EC_{50}$=42 nM (n=2), DNA content $EC_{50}$=40 nM (n=2) and mitotic $EC_{50}$=45 nM (n=1).

Antiproliferative Assay

The effects of compounds on cell proliferation can be determined using cells and cell proliferation methods well-known in the art (Robert C. Squatrito et al., Gynecological Oncology, 58, 101-105, (1995)). For example, HCT116 cells, which may be obtained from the American Type Culture Collection, may be seeded at 2000 cells/well in 96-well plates and allowed to attach overnight in a humidified $CO_2$ incubator at 37° C. Following the 20-24 hour incubation, half-log serially diluted compounds are added and the plates are returned to the incubator. After an appropriate length of exposure (e.g., 72 hours), cell proliferation is estimated using well-known methods. In one method, 10 μL of a tetrazolium salt, such as Alamar Blue™ is added to the cell plates. After an appropriate exposure to the dye, fluorescence (530 nm excitation, 580 nm emission) is determined. The resulting $IC_{50}$ has an MSR of 3.1. For example, Example 13 has an $IC_{50}$ of 11 nM (n=3).

The compounds of the present invention are preferably formulated as pharmaceutical compositions administered by a variety of routes. Most preferably, such compositions are for oral administration. Such pharmaceutical compositions and processes for preparing same are well known in the art. See, e.g., REMINGTON: THE SCIENCE AND PRACTICE OF PHARMACY (A. Gennaro, et al., eds., 19th ed., Mack Publishing Co., 1995).

The compounds of Formula I are generally effective over a wide dosage range. For example, dosages per day normally fall within the range of about 0.01 to about 20 mg/kg of body weight, more preferably 0.1 to 20 mg/kg of body weight. In some instances dosage levels below the lower limit of the aforesaid range may be more than adequate, while in other cases still larger doses may be employed without causing any harmful side effect, and therefore the above dosage range is not intended to limit the scope of the invention in any way. It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

We claim:
1. A compound of the formula:

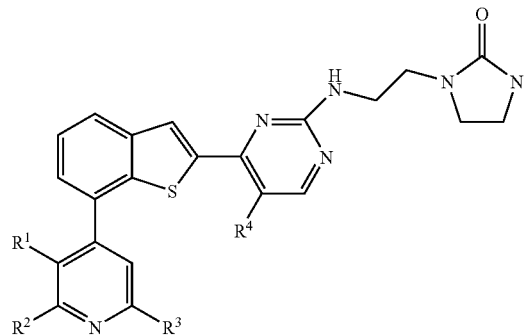

wherein:
$R^1$ is hydrogen, hydroxy, hydroxymethyl, halo, methyl, fluoromethyl, $C_1$-$C_2$ alkoxy, amino, or methylamino;
$R^2$ is hydrogen, halo, or cyano;
$R^3$ is hydrogen or halo; provided that at least one of $R^1$, $R^2$, and $R^3$ is hydrogen;
and $R^4$ is hydrogen, halo, or methyl; or a pharmaceutically acceptable salt thereof.

2. The compound of claim 1 wherein:
$R^1$ is hydrogen, hydroxy, hydroxymethyl, chloro, fluoro, methyl, fluoromethyl, $C_1$-$C_2$ alkoxy, amino, or methylamino;
$R^2$ is hydrogen, fluoro, or cyano;
$R^3$ is hydrogen chloro, or fluoro;
provided that at least one of $R^1$, $R^2$, and $R^3$ is hydrogen; and $R^4$ is hydrogen, chloro, fluoro, or methyl; or a pharmaceutically acceptable salt thereof.

3. The compound of claim 1 wherein:
$R^1$ is hydrogen, methyl, or fluoromethyl;
$R^2$ is hydrogen or fluoro;
$R^3$ is hydrogen chloro, or fluoro;
provided that at least one of $R^1$, $R^2$, and $R^3$ is hydrogen; and $R^4$ is hydrogen, chloro, fluoro, or methyl; or a pharmaceutically acceptable salt thereof.

4. The compound of claim 1 wherein $R^1$ is halo, $R^2$ is hydrogen, $R^3$ is halo, and $R^4$ is halo; or a pharmaceutically acceptable salt thereof.

5. A compound selected from the group consisting of:
1-(2-{4-[7-(2-Chloro-pyridin-4-yl)-benzo[b]thiophen-2-yl]pyrimidin-2-ylamino}ethyl)imidazolidin-2-one,
1-(2-{5-Fluoro-4-[7-(2-fluoro-5-methylpyridin-4-yl)-benzo[b]thiophen-2-yl]-pyrimidin-2-ylamino}ethyl) imidazolidin-2-one, 1-(2-{4-[7-(2-Fluoro-5-methylpyridin-4-yl)-benzo[b]
thiophen-2-yl]-5-methylpyrimidin-2-ylamino}ethyl)
imidazolidin-2-one, 1-(2-{4-[7-(2-Fluoro-5-methylpyridin-4-yl)-benzo[b]
thiophen-2-yl]pyrimidin-2-ylamino)-ethyl)imidazolidin-2-one, 1-{2-[5-Methyl-4-(7-pyridin-4-yl-benzo[b]thiophen-2-yl)pyrimidin-2-ylamino]-ethyl}imidazolidin-2-one, 1-(2-{5-Chloro-4-[7-(2-fluoro-5-methylpyridin-4-yl)
benzo[b]thiophen-2-yl]-pyrimidin-2-ylamino}ethyl)
imidazolidin-2-one, 1-{2-[5-Fluoro-4-(7-pyridin-4-yl-benzo[b]thiophen-2-yl)
pyrimidin-2-ylamino]-ethyl}imidazolidin-2-one, 1-(2-{4-[7-(3-Ethoxypyridin-4-yl)-benzo[b]thiophen-2-
yl]-5-fluoropyrimidin-2-ylamino}ethyl)imidazolidin-2-one, 1-(2-(5-Fluoro-4-(7-(3-hydroxypyridin-4-yl)benzo[b]
thiophen-2-yl)pyrimidin-2-ylamino)ethyl)imidazolidin-2-one, 1-(2-{4-[7-(2-Chloro-5-ethoxypyridin-4-yl)-benzo[b]
thiophen-2-yl]-5-fluoropyrimidin-2-ylamino}-ethyl)
imidazolidin-2-one, 1-(2-{5-Fluoro-4-[7-(3-methoxypyridin-4-yl)-benzo[b]
thiophen-2-yl]pyrimidin-2-ylamino}-ethyl)imidazolidin-2-one, 1-(2-(5-Chloro-4-(7-(pyridin-4-yl)benzo[b]thiophen-2-yl)pyrimidin-2-ylamino)ethyl)imidazolidin-2-one, 1-(2-{5-Chloro-4-[7-(5-chloro-2-fluoropyridin-4-yl)-
benzo[b]thiophen-2-yl]pyrimidin-2-ylamino}ethyl)
imidazolidin-2-one, 1-(2-{4-[7-(2-Chloro-pyridin-4-yl)-benzo[b]thiophen-2-
yl]-5-fluoropyrimidin-2-ylamino}ethyl)imidazolidin-2-one, 1-(2-{5-Chloro-4-[7-(2-chloro-pyridin-4-yl)benzo[b]
thiophen-2-yl]pyrimidin-2-ylamino}ethyl)imidazolidin-2-one, 1-(2-{4-[7-(5-Chloro-2-fluoro-pyridin-4-yl)-benzo[b]
thiophen-2-yl]-5-fluoropyrimidin-2-ylamino}ethyl)
imidazolidin-2-one, 1-(2-{4-[7-(2-Chloro-5-fluoropyridin-4-yl)-benzo[b]
thiophen-2-yl]-5-fluoropyrimidin-2-ylamino}-ethyl)
imidazolidin-2-one, 1-(2-{4-[7-(3-Chloro-pyridin-4-yl)-benzo[b]thiophen-2-
yl]-5-fluoropyrimidin-2-ylamino}ethyl)imidazolidin-2-one, 1-(2-{5-Fluoro-4-[7-(3-methylpyridin-4-yl)-benzo[b]
thiophen-2-yl]pyrimidin-2-ylamino}ethyl)imidazolidin-2-one, 1-(2-{4-[7-(5-Chloro-2-fluoropyridin-4-yl)-benzo[b]
thiophen-2-yl]-5-methylpyrimidin-2-ylamino}ethyl)
imidazolidin-2-one, 1-(2-{4-[7-(2,5-Dichloropyridin-4-yl)-benzo[b]thiophen-
2-yl]-5-fluoropyrimidin-2-ylamino}ethyl)imidazolidin-2-one, 1-(2-{5-Fluoro-4-[7-(2-fluoropyridin-4-yl)-benzo[b]
thiophen-2-yl]pyrimidin-2-ylamino}ethyl)imidazolidin-2-one, 1-(2-{4-[7-(5-Chloro-2-fluoro-pyridin-4-yl)-benzo[b]
thiophen-2-yl]pyrimidin-2-ylamino}ethyl)imidazolidin-2-one, 4-(2-(2-(2-(2-oxoimidazolidin-1-yl)ethylamino)pyrimidin-4-yl)benzo[b]thiophen-7-yl)picolinonitrile, 1-(2-{4-[7-(3-Amino-pyridin-4-yl)benzo[b]thiophen-2-
yl]-5-fluoropyrimidin-2-ylamino}ethyl)imidazolidin-2-one, 1-(2-{4-[7-(3-Methylamino-pyridin-4-yl)benzo[b]
thiophen-2-yl]pyrimidin-2-ylamino}ethyl)imidazolidin-2-one, 1-(2-{4-[7-(3-Amino-pyridin-4-yl)benzo[b]thiophen-2-
yl]-5-methylpyrimidin-2-ylamino}ethyl)imidazolidin-2-one, 1-(2-{4-[7-(3-Amino-pyridin-4-yl)benzo[b]thiophen-2-
yl]-pyrimidin-2-ylamino}ethyl)imidazolidin-2-one, 1-(2-{4-[7-(5-Amino-2-fluoropyridin-4-yl)benzo[b]
thiophen-2-yl]pyrimidin-2-ylamino}ethyl)imidazolidin-2-one, 1-(2-{4-[7-(3-Amino-2-fluoropyridin-4-yl)benzo[b]
thiophen-2-yl]pyrimidin-2-ylamino}ethyl)imidazolidin-2-one, 1-(2-{5-Fluoro-4-[7-(2-fluoro-5-hydroxymethyl-pyridin-4-yl)benzo[b]thiophen-2-yl]pyrimidin-2-ylamino}ethyl)imidazolidin-2-one, and 1-(2-{5-Fluoro-4-[7-(2-fluoro-5-(fluoromethyl)pyridin-4-yl)benzo[b]thiophen-2-yl]pyrimidin-2-ylamino}ethyl)imidazolidin-2-one; or a pharmaceutically acceptable salt.

6. A pharmaceutical composition comprising a compound of claim 1 or a pharmaceutically acceptable salt thereof, in combination with a pharmaceutically acceptable carrier, diluent or excipient.

* * * * *

UNITED STATES PATENT AND TRADEMARK OFFICE
CERTIFICATE OF CORRECTION

PATENT NO. : 8,101,628 B2
APPLICATION NO. : 12/516514
DATED : January 24, 2012
INVENTOR(S) : Joyce Z. Crich et al.

It is certified that error appears in the above-identified patent and that said Letters Patent is hereby corrected as shown below:

Title Page, Column 1, item 75 (Inventors): Delete first inventor "Harold Burns Brooks, Carmel, IN (US);".

Title Page, Column 1, before item 51, insert -- (60) Related U.S. Application Data, Provisional Application No. 60/871,302, filed December 21, 2006 --.

At Column 36, Line 48: In Claim 2, delete "hydrogen chloro," and insert -- hydrogen, chloro, -- therefor.

At Column 36, Line 55: In Claim 3, delete "hydrogen chloro," and insert -- hydrogen, chloro, -- therefor.

Signed and Sealed this
Twentieth Day of March, 2012

David J. Kappos
*Director of the United States Patent and Trademark Office*